US008703488B2

(12) United States Patent
Impola et al.

(10) Patent No.: US 8,703,488 B2
(45) Date of Patent: *Apr. 22, 2014

(54) CULTURE OF CELLS

(75) Inventors: Ulla Impola, Helsinki (FI); Minna Tiittanen, Helsinki (FI); Milla Mikkola, Helsinki (FI); Jukka Partanen, Helsinki (FI); Jari Natunen, Vantaa (FI); Tero Satomaa, Helsinki (FI); Juhani Saarinen, Helsinki (FI)

(73) Assignees: Suomen Punainen Risti Veripalvelu, Helsinki (FI); Glykos Finland Oy, Helsinki (FI)

( * ) Notice: Subject to any disclaimer, the term of this patent is extended or adjusted under 35 U.S.C. 154(b) by 97 days.

This patent is subject to a terminal disclaimer.

(21) Appl. No.: 13/003,493

(22) PCT Filed: Jul. 13, 2009

(86) PCT No.: PCT/FI2009/050624
§ 371 (c)(1),
(2), (4) Date: Sep. 1, 2011

(87) PCT Pub. No.: WO2010/004096
PCT Pub. Date: Jan. 14, 2010

(65) Prior Publication Data
US 2011/0306128 A1 Dec. 15, 2011

Related U.S. Application Data

(63) Continuation-in-part of application No. 12/171,866, filed on Jul. 11, 2008, now abandoned.

(30) Foreign Application Priority Data

Jul. 11, 2008 (FI) .................................... 20085724

(51) Int. Cl.
*C12N 5/00* (2006.01)
*C12N 5/02* (2006.01)
*C12N 5/071* (2010.01)

(52) U.S. Cl.
USPC ............ 435/402; 435/366; 435/395; 435/401

(58) Field of Classification Search
USPC .................................. 435/366, 395, 401, 402
See application file for complete search history.

(56) References Cited

U.S. PATENT DOCUMENTS

| 4,963,469 | A | 10/1990 | Mattes et al. |
| 6,251,383 | B1 | 6/2001 | Upadhyay et al. |
| 2004/0121301 | A1 | 6/2004 | Kato et al. |
| 2005/0060779 | A1 | 3/2005 | Colucci et al. |
| 2006/0177413 | A1 | 8/2006 | Kalovidouris et al. |
| 2010/0068806 | A1 | 3/2010 | Laine et al. |

FOREIGN PATENT DOCUMENTS

| EP | 1 674 566 A1 | 6/2006 |
| WO | WO 2004/055155 A2 | 7/2004 |
| WO | WO 2006/117671 A2 | 11/2006 |
| WO | WO 2007/002086 A2 | 1/2007 |
| WO | WO 2007/006870 A2 | 1/2007 |
| WO | WO 2007/054620 A1 | 5/2007 |
| WO | WO 2007/054622 A1 | 5/2007 |
| WO | WO 2007/066352 A1 | 6/2007 |
| WO | WO 2008/000918 A1 | 1/2008 |
| WO | WO 2008/008550 A2 | 1/2008 |

OTHER PUBLICATIONS

R&D systems (accessed online at http://www.rndsystems.com/cb_detail_objectname_SU02_Galectins.aspx on Feb. 10, 2012.*
Aalto et al., "Mutant bacteriophage with non-catalytic endosialidase binds to both bacterial and eukaryotic polysialic acid and can be used as probe for its detection", Glycoconjugate Journal 18, pp. 751-758, 2001.
Advisory Action dated Oct. 20, 2011 for U.S. Appl. No. 12/171,866.
Brevini et al. "No Shortcuts to Pig Embryonic Stem Cells", Theriogenology, vol. 74, pp. 544-550, (2010).
Cao et al., "Isolation and Culture of Primary Bovine Embryonic Stem Cell Colonies by a Novel Method", Journal of Experimental Zoology, vol. 311A., pp. 368-376, (2009).
Finland Search Report dated Nov. 19, 2007 for Finland Application No. 20075034.
Finland Search Report dated Oct. 30, 2007 for Finland Application No. 20075033.
Gunnarsson et al., "Engineered xyloglucan specificity in a carbohydrate-binding module", Glycobiology, vol. 16, No. 12, pp. 1171-1180, 2006.
International Preliminary Report on Patantability dated Apr. 27, 2009 for International Application No. PCT/FI2008/050016.
International Search Report dated Feb. 3, 2010 for Application No. PCT/FI2009/050624.
International Search Report dated Jun. 17, 2008 for International Application No. PCT/FI2008/050016.
Kannagi et al., "Stage-specific embryonic antigens (SSEA-3 and -4) are epitopes of a unique globo-series ganglioside isolated from human teratocarcinoma cells," The EMBO Journal, vol. 2, No. 12, pp. 2355-2361, 1983.
Miyazaki et al., "Recombinant human laminin isoforms can support the undifferentiated growth of human embryonic stem cells", Biochemical and Biophysical Research Communications, vol. 375, 2008, pp. 27-32.

(Continued)

*Primary Examiner* — Thaian N Ton
(74) *Attorney, Agent, or Firm* — Birch, Stewart, Kolasch & Birch, LLP

(57) ABSTRACT

The invention relates to a method for culturing human embryonic stem cells (hESCs) and/or induced pluripotent stem (iPS) cells on a lectin. The invention relates also to the use of a lectin in a method for culturing human embryonic stem cells (hESCs) and/or induced pluripotent stem (iPS) celts and a culture medium composition containing a lectin attached on the culturing plates.

11 Claims, 11 Drawing Sheets

(56) References Cited

OTHER PUBLICATIONS

Paris et al., "Equine Embryos and Embryonic Stem Cells: Defining Reliable Markers of Pluripotency", Theriogenology, vol. 74, pp. 516-524, (2010).

Rajala et al., "A Defined and Xeno-Free Culture Method Enabling the Establishment of Clinical-Grade Human Embryonic, Induced Pluripotent and Adipose Stem Cells", PLoS one, vol. 5, No. 4, pp. 1-14, 2010.

Takahashi et al., "Induction of Pluripotent Stem Cells from Adult Human Fibroblasts by Defined Factors", Cell 131, pp. 1-12, 2007.

US Office Action dated Aug. 11, 2011 for U.S. Appl. No. 12/171,866.

US Office Action dated Dec. 30, 2010 for U.S. Appl. No. 12/171,866.

"Serum- and feeder-free media", STEMPRO hESC SFM, Human Embryonic Stem Cell Culture Medium, Stem Cell Research, Stem Pro® product guide, from the Invitrogen catalog, pp. 1-6, (2007).

Donaldson et al., "The Use of Lectins to Select Subpopulations of Insect Cells", Biotechnol. Bioeng, vol. 64, pp. 616-619, (1999).

He et al., "Galectin Interactions with Extracellular Matrix and Effects on Cellular Function", Methods in Enzymology, vol. 417, pp. 247-256, (2006).

Ideo et al., "Galectin-4 Binds to Sulfated Glycosphingolipids and Carcinoembryonic Antigen in Patches on the Cell Surface of Human Colon Adenocarcinoma Cells", The Journal of Biological Chemistry, vol. 280, No. 6, pp. 4730-4737, (2005).

International Search Report, PCT/FI2009/050624, Feb. 3, 2010, pp. 1-5.

Lim et al., "Proteome analysis of conditioned medium from mouse embryonic fibroblast feeder layers which support the growth of human embryonic stem cells", Proteomics, vol. 2, pp. 1187-1203, (2002).

Ludwig et al., "Brief Communications", Nature Biotechnolgy, vol. 24, No. 2, pp. 185-187, (Feb. 2006).

Mallon et al., "Toward xeno-free culture of human embryonic stem cells", The International Journal of Biochemistry & Cell Biology, vol. 38, pp. 1063-1075 (2006).

Mikkola et al., "Distinct differentiation characteristics of individual human embryonic stem cell lines", BMC Developmental Biology, vol. 6, No. 40, p. 1-11, (Aug. 8, 2006).

Muramatsu et al., "Carbohydrate antigens expressed on stem cells and early embryonic cells", Glycoconjugate Journal, Jan., 2004, vol. 21, Nos. 1-2, pp. 41-45, XP-019206995.

Oh et al., "Clinical and Experimental Pharmacology & Physiology", vol. 33, pp. 489-495, (2006).

Okita et al., "Generation of germline-competent induced pluripotent stem cells", nature, vol. 448, pp. 313-318, (Jul. 19, 2007).

Prowse et al., "A proteome analysis of conditioned media from human neonatal fibroblasts used in the maintenance of human embryonic stem cells", Proteomics, vol. 5, pp. 978-989, (2005).

Satomaa at al., "The N-glycome of human embryonic stem cells", BMC Cell Biology, vol. 10, No. 42, pp. 1-18, (Jun. 2, 2009).

Search Report issued May 7, 2009 in corresponding Finnish application No. 20085724.

Thomson et al. "Isolation of a primate embryonic stem cell line", PNAS, vol. 92, pp. 7844-7848, (Aug. 1995).

Vas et al., "Biphasic Effect of Recombinant Galectin-1 on the Growth and Death of Early Hematopoietic Cells", Stem Cells, Feb., 2005, vol. 23, No. 2: pp. 279-287. XP-002563291.

Venable et al., "Lectin binding profiles of SSEA-4 enriched, pluripotent human embryonic stem cell surfaces", BMC Developmental Biology, vol. 5, No. 15, pp. 1-11, (Jul. 21, 2005).

Wearne et al., "Use of lectins for probing differentiated human embryonic stem cells for carbohydrates", Glycobiology, vol. 16, No. 10, pp. 981-990, Oxford University Press, 2006.

\* cited by examiner

CLUSTAL 2.0.8 multiple sequence alignment

```
ECA|1UZY|A                    ---------------------------------------VETISFSFSEFEP  13
ECO|1AX0|A                    ---------------------------------------VETISFSFSEFEP  13
Erythrina_variegata           ---------------------------------------VETISFSFSEFEA  13
WBAI|O24313.1|LEC1_PSOTE      ---------------------------------------MKTISFNFNQFHQ  13
WBAII|1FAY|A                  ----------------------------------------ETQSFNFDHFEE  12
Phaseluna|CAA93830.1|         --------------GL---------ALFLVLLNHANSTDLFSFNFQTFH-  26
PhaseAugusti|CAH59200.1|      ----MASSKFCTVLSL---------ALFLVLLTHANSAELFSFNFQTFN-  36
Phasemacu|CAH60256.1|         ----MASSNFSTVLSL---------ALFLVLLTHANSTNLFSFNFQKFH-  36
PhaseLepto|CAH60214.1|        ----MASSNFSTVFSL---------ALFLVLLTQANSTDLFSFNFQKFH-  36
PhaseVulg|CAD28674.1|         ----MASS---KLLSL---------ALFLVLLTLANSASETSFSFQRFS-  33
Soy|2SBA|A                    -----------------------------------AETVSFSWNKFVP   13
Robinia|BAA36415.1|           ----MATSNLQTLKSLFFVLLSISLTFFLLLPNKVNSTESVSFSFTKFVP  46
Maackia|AAB39934.1|           ---------ATSNSKPTQVLLATFLTFFFLLLNNVNSDELSFTINNFVP   41
UlexII|AAG16779.1|            ----------------------------------NSSDDLSFNFDKFVP  15
UlexGene1Ulex                 -------------------------------------DDLSFKFKNFSQ  12
UlexI|1FX5|A                  ------------------------------------SDDLSFKFKNFSQ  13
SOPJA|P93535.1|LECS_SOPJA     MATSNSRPHLLQTHKPFSVVLAISITFFLLLLNKVNSAEILSFSFPKFAS  50
                                                                    . **.    *

ECA|1UZY|A                    GNNDLTLQGAAIITQSGVLQLTKINQNGMPAWDSTGRTLYTKPVHIWDMT  63
ECO|1AX0|A                    GNDNLTLQGAALITQSGVLQLTKINQNGMPAWDSTGRTLYAKPVHIWDMT  63
Erythrina_variegata           GNDNLTLQGAALITQSGVLQLTKINQNGMPAWNSTGRTLYSKPVHIWDKT  63
WBAI|O24313.1|LEC1_PSOTE      NEEQLKLQRDARISSNSVLELTKVVN-GVPTWNSTGRALYAKPVQVWDST  62
WBAII|1FAY|A                  NSKELNLQRQASIKSNGVLELTKLTKNGVPVWKSTGRALYAEPIKIWDST  62
Phaseluna|CAA93830.1|         -EANLILQGNASVSSSGQLRLTEVKSNGEPEVASLGRAFYSAPIQIWDST  75
PhaseAugusti|CAH59200.1|      -EANLILQGNASVSSSGQLRLTEVKSNGVPEVASLGRAFYSAPIQIWDST  85
Phasemacu|CAH60256.1|         -EPNLILQGNASVSSSGQLRLTEVKSNGEPEVASLGRAFYSAPIQIWDNT  85
PhaseLepto|CAH60214.1|        -SHNLILQGDASVSSSGQLRLTGVKSNGEPKVASLGRVFYSAPIQIWDNT  85
PhaseVulg|CAD28674.1|         -SSNLILQGNASVSSSGQLRLTNLNGNGEPRVGSLGRAFYSAPIQIWDKT  82
Soy|2SBA|A                    KQPNMILQGDAIVTSSGKLQLNKVDENGTPKPSSLGRALYSTPIHIWDKE  63
Robinia|BAA36415.1|           EEQNLILQGDAQVRPTGTLELTKVET-GTPISNSLGRALYAAPIRIYDNT  95
Maackia|AAB39934.1|           NEADLLFQGEASVSSTGVLQLTRVEN-GQPQQYSVGRALYAAPVRIWDNT  90
UlexII|AAG16779.1|            NQKNIIFQGAASVSTTGVLQVTKVS---KPTTTSIGRALYAAPIQIWDST  62
UlexGene1Ulex                 NGKDLTFQGNASVLETGVLQLNKVGN-NLPDETG-GIARYIAPIHIWNNN  60
UlexI|1FX5|A                  NGKDLSFQGNASVIETGVLQLNKVGN-NLPDETG-GIARYIAPIHIWNCN  61
SOPJA|P93535.1|LECS_SOPJA     NQEDLLLQGDALVSSKGELQLTTVEN-GVPIWNSTGRALYYAPVHIWDKS  99
                               ::  :*   *  :    .. *.:. :       *   . * . * *:::::

ECA|1UZY|A                    TGTVASFETRFSFSIEQPYTRPLPADGLVFFMGPTKSK--PAQGYGYLGV 111
ECO|1AX0|A                    TGTVASFETRFSFSIEQPYTRPLPADGLVFFMGPTKSK--PAQGYGYLGI 111
Erythrina_variegata           TGTVASFETRFSFSIEQPYTRPLPADGLVFFMGPTKSK--PAQGYGYLGV 111
WBAI|O24313.1|LEC1_PSOTE      TGNVASFETRFSFSIRQPFPRPHPADGLVFFIAPPNTQ--TGEGGGYFGI 110
WBAII|1FAY|A                  TGNVASFETRFSFSIKQPYAYPEPADGLTFFMVPPNSP--QGEDGGNLGV 110
Phaseluna|CAA93830.1|         TGKVASFATSFTFNILAP-ILSNSADGLAFALVPVGSQ--PKFNGGFLGL 122
PhaseAugusti|CAH59200.1|      TGKVASFATAFTFNILAP-ILSNSADGLAFALVPVGSQ--PKFNGGFLGL 132
Phasemacu|CAH60256.1|         TGNVASFATSFTFNILSP-TISKSADGLAFALVPVGSQ--PKTYGGYLGL 132
PhaseLepto|CAH60214.1|        TGNVASFATSFTFNILAP-TVSKSADGLAFALVPVGSQ--PKSDGGYLGL 132
PhaseVulg|CAD28674.1|         TGTVASFATSFTFNMQVP-NNAGPADGLAFALVPVGSQ--PKDKGGFLGL 129
Soy|2SBA|A                    TGSVASFAASFNFTFYAP-DTKRLADGLAFFLAPIDTK--PQTHAGYLGL 110
Robinia|BAA36415.1|           TGNLASFVTSFSFNIKAP-NRFNAAEGLAFFLAPVNTK--PQSPGGLLGL 142
Maackia|AAB39934.1|           TGSVASFSTSFTFVVK-APNPTITSDGLAFFLAPPDSQIPSGRVSKYLGL 139
UlexII|AAG16779.1|            TGKVASFATSFSFVVK-ADK-SDGVDGLAFFLAPANSQIPSGSSASMFGL 110
UlexGene1Ulex                 TGEVASFITSFSFSFMETSSNPKAATDGLTFFLAPPDS--PLRRAGGYFGL 108
UlexI|1FX5|A                  TGELASFITSFSFFMETSANPKAATDGLTFFLAPPDS--PLRRAGGYFGL 109
SOPJA|P93535.1|LECS_SOPJA     TGRVASFATSFSFVVK-APVASKSADGIAFFLAPPNNQ-IQGPGGGHLGL 147
                              **  :*** :  *.*  .        :*:..* : *     .       :*:
```

Figure 9

```
ECA|1UZY|A                    FRNSKQDNSYQTLAVEFDT---FSN-PWDPPQVPHIGIDVNSIRSIKTQP 157
ECO|1AXO|A                    FRNSKQDNSYQTLGVEFDT---FSN-PWDPPQVPHIGIDVNSIRSIKTQP 157
Erythrina_variegata           FRNSKQDNSYQTLAVEFDT---FSN-PWDPPQGPHIGIDVNSIRSIKTQP 157
WBAI|O24313.1|LEC1_PSOTE      YNPLSPYP---FVAVEFDT---FRN-TWDP-QIPHIGIDVNSVISTKTVP 152
WBAII|1FAY|A                  FKPPEGDN---AFAVEFDT---FQN-TWDP-QVPHIGIDVNSIVSSKTLH 152
Phaseluna|CAA93830.1|         FERATYDPTARTVAVEFDT---CFNLDWDP-KGPHIGIDVNSIKSIKTVP 168
PhaseAugusti|CAH59200.1|      FQRVTYDPTAQTVAVEFDT---CHNLDWDP-KGPHIGIDVNSIKSIKTVP 178
Phasemacu|CAH60256.1|         FQHATNDPTAQTVAVEFDT---FFNREWDP-EGHHIGIDVNSIKSMKTVP 178
PhaseLepto|CAH60214.1|        FESATYDPTAQTVAVEFDT---FFNQKWDP-EGRHIGIDVNSIKSVKTAP 178
PhaseVulg|CAD28674.1|         FDGSNSN--FHTVAVEFDT---LYNKDWDP-RERHIGIDVNSIRSIKTTP 173
Soy|2SBA|A                    FNERESG--DQVVAVEFDT---FRN-SWDP-PNPHIGINVNSIRSIKTTS 153
Robinia|BAA36415.1|           FKDKEFDKSNQIVAVEFDT---FFNEEWDP-QGSHIGIDVNSINSVKTTR 188
Maackia|AAB39934.1|           FRNSNSDSSNQIVAVEFDTYFGHSYDPWDP-NYRHIGIDVNGIESIKTVQ 188
UlexII|AAG16779.1|            FSSDSKSSNQIIAVEFDTYFGKAYNPWDP-DFKHIGIDVNSIKSIKTVK 159
UlexGene1Ulex                 FNDTKCDSSYQTVAVEFDT-IGSPVNSWDP-GFPHIGIDVNCVISINAER 156
UlexI|1FX5|A                  FNDTKCDSSYQTVAVEFDT-IGSPVNFWDP-GFPHIGIDVNCVKSINAER 157
SOPJA|P93535.1|LECS_SOPJA     FHSSGYRSSYQIIAVDFDT----HINAWDP-NTRHIGIDVNSINSTKTVT 192
                              :.      ..*:***      ***     ****:**  :  *  ::

ECA|1UZY|A                    FQLDNG--QVANVVIKYDASSKILLAVLVYPSSGAIYTIAEIVDVKQVLP 205
ECO|1AXO|A                    FQLDNG--QVANVVIKYDASSKILHAVLVYPSSGAIYTIAEIVDVKQVLP 205
Erythrina_variegata           FQLDNG--QVANVVIKYDASSKILHAVLVYPSNGAIYTIAEIVDVKEVLP 205
WBAI|O24313.1|LEC1_PSOTE      FTLDNG--GIANVVIKYDASTKILHVVLVFPSLGTIYTIADIVDLKQVLP 200
WBAII|1FAY|A                  FQLENG--GVANVVIKYDSPTKILNVVLAFHSVGTVYTLSNIVDLKQEFP 200
Phaseluna|CAA93830.1|         WSLLNG--HNAKVLITYDSSTKLLVASLVYPSGSTSYIISEKVDLKSVLP 216
PhaseAugusti|CAH59200.1|      WSLLNG--HNAKVLITYDSSTKLLVASLVYPSGSTSYIISEKVELKSVLP 226
Phasemacu|CAH60256.1|         WDFLNG--HNAEVLITYDSSTNLLVASLVYPSGAMS-CISERVVLKSVLP 225
PhaseLepto|CAH60214.1|        WGLLNG--HKAEILITYDSSTNLLVASLVHPAGATSHIVSERVELKSVLP 226
PhaseVulg|CAD28674.1|         WNFVNG--ENAEVLITYDSSTKLLVASLVYPSQKTSFIVSDTVDLKSVLP 221
Soy|2SBA|A                    WDLANN--KVAKVLITYDASTSLLVASLVYPSQRTSNILSDVVDLKTSLP 201
Robinia|BAA36415.1|           FALANG--NVANVVITYEASTKTLTAFLVYPARQTSYIVSSVVDLQDVLP 236
Maackia|AAB39934.1|           WDWING--GVAFATITYLAPNKTLIASLVYPSNQTSFIVAASVDLKEILP 236
UlexII|AAG16779.1|            WDWRNG--EVADVVITYRAPTKSLTVCLSYPSDETSNIITASVDLKAILP 207
UlexGene1Ulex                 WNKRYGSNNVANVEIIYEASSKTLTASLTYPSDQTSISVTSIVDLKEILP 206
UlexI|1FX5|A                  WNKRYGLNNVANVEIIYEASSKTLTASLTYPSDQTSISVTSIVDLKEILP 207
SOPJA|P93535.1|LECS_SOPJA     WGWQNG--EVANVLISYQAATETLTVSLTYPSSQTSYILSAAVDLKSILP 240
                              :   .    *  * *  ... *  . * .:    ::  *  ::   :*

ECA|1UZY|A                    EW--VDVGLSGATG----AQRDAAETHDVYSWSFHASLPETND------- 242
ECO|1AXO|A                    EW--VDVGLSGATG----AQRDAAETHDVYSWSFQASLPE---------- 239
Erythrina_variegata           EW--VDVGLSGATG----AQRDAAETHDVYSWSFHASLPETN-------- 241
WBAI|O24313.1|LEC1_PSOTE      ES--VNVGFSAATGDPSGKQRNATETHDILSWSFSASLPGTNEF------ 242
WBAII|1FAY|A                  NSEWVNVGLSATTG----YQRNAVETHEIISWSFTSSLQETN-------- 238
Phaseluna|CAA93830.1|         EW--VNIGFSATSG----LNKGNVETHDVLSWSFASKLSDGTP-CEGLSL 259
PhaseAugusti|CAH59200.1|      EW--VNIGFSATSG----LNKGNVETHDVLSWSFASKLSDGTT-CEGLSL 269
Phasemacu|CAH60256.1|         EW--VNIGFSATSG----LNKGYVETHDVLSWSFASELSAGTT-SEGLSL 268
PhaseLepto|CAH60214.1|        EW--VSIGFSATSG----LSKGFVEIHDVLSWSFASKLSNETT-SEGLSL 269
PhaseVulg|CAD28674.1|         EW--VNIGFSATSG----INKGNVETHDVLSWSFASKLSDGTT-SEGLNL 264
Soy|2SBA|A                    EW--VRIGFSAATG----LDIP-GESHDVLSWSFASNLPHASSNIDPLDL 244
Robinia|BAA36415.1|           QF--VDVGFSATTG----LSEGLVESHDILSWSFHSNLPDSSS----DAL 276
Maackia|AAB39934.1|           EW--VRVGFSAATG----YPTQV-ETHDVLSWSFTSTLEANSDAATENN- 278
UlexII|AAG16779.1|            EW--VSVGFSGGVG----NAAEF-ETHDILSWYFTSNLEANNPAAMEYND 250
UlexGene1Ulex                 EW--VSVGFSGTT-----YIGRQ-ATHEVLNWYFSSTFDPNNN------- 241
UlexI|1FX5|A                  EW--VSVGFSGST-----YIGRQ-ATHEVLNWYFTSTFINTNS------- 242
SOPJA|P93535.1|LECS_SOPJA     EW--VRVGFTAATG----LTTQYVETHDVLSWSFTSTLETGDCGAKDDN- 283
                              :    * :*::.            :::   .*  *  :  :
```

Figure 9 (cont.)

```
ECA|1UZY|A                   ---------
ECO|1AX0|A                   ---------
Erythrina_variegata          ---------
WBAI|O24313.1|LEC1_PSOTE     ---------
WBAII|1FAY|A                 ---------
Phaseluna|CAA93830.1|        ANIVLNKIL 268
PhaseAugusti|CAH59200.1|     ANIVLNQIL 278
Phasemacu|CAH60256.1|        ANIVLNKIL 277
PhaseLepto|CAH60214.1|       ANIVLNKIL 278
PhaseVulg|CAD28674.1|        ANLVLNKIL 273
Soy|2SBA|A                   TSFVLHEAI 253
Robinia|BAA36415.1|          ANNILRDFM 285
Maackia|AAB39934.1|          VHIARYTA- 286
UlexII|AAG16779.1|           EHLASFTA- 258
UlexGene1Ulex                ---------
UlexI|1FX5|A                 ---------
SOPJA|P93535.1|LECS_SOPJA    VHLVSYAFI 292
```

CULTURE OF CELLS

This application is the National Phase of PCT/FI2009/050624 filed on Jul. 13, 2009, and claims priority under 35 U.S.C. 120 to, and is a Continuation-in-Part of, U.S. patent application Ser. No. 12/171,866 filed on Jul. 11, 2008. The present application also claims priority to Patent Application No. 20085724 filed in Finland on Jul. 11, 2008, all of which are hereby expressly incorporated by reference into the present application.

FIELD OF THE INVENTION

The invention relates to a method for culturing human embryonic stem cells (hESCs) and/or induced pluripotent stem (iPS) cells on a lectin. The invention relates also to the use of a lectin in a method for culturing human embryonic stem cells (hESCs) and/or induced pluripotent stem (iPS) cells and a culture medium composition containing a lectin attached on the culturing plates.

BACKGROUND OF THE INVENTION

Traditional methods for culturing human embryonic stem cells (hESCs) require the direct use of mouse embryonic fibroblasts (MEFs) as a feeder layer, or feeder-conditioned medium or serum. A medium for a feeder-free culture of hESCs includes an extracellular matrix extracted from a mouse sarcoma and is sold under the trademark Matrigel™ (BD Bioscience, US). Matrigel™ is mostly comprised of laminin and collagen and these compounds in purified form have also been tried in culturing hESCs.

Matrigel™ and the other feeder-free media used currently in cultures suffer from xeno contamination, and in addition are subject to large variability caused by containing growth factors and other undefined molecules.

Mallon B. S. et al. have reviewed the attempts made toward xenofree culture of hESCs in The International Journal of Biochemistry and Cell Biology 38, 1063-1075, 2006. As can be concluded, the culture of hESCs suffers with respect to both technical and clinical potential by the use of cells or extracts originating from animal sources, such as mouse embryonic fibroblasts and an extract from a mouse sarcoma. The current culture methods are also laborious and difficult to scale. Further, it is often hard to maintain the cells in uniform quality and in an undifferentiated form.

One of the biggest problems of the current methods and media for culturing hESCs and embryonic stem cell-like cells, such as iPS cells, arises from the use of animal-derived material in the culture medium.

This problem has now been solved in accordance of the present invention by providing a method for culturing hESCs and/or iPS cells using a medium containing a lectin as a culturing matrix.

BRIEF DESCRIPTION OF THE INVENTION

The present invention is directed to a method for culturing human embryonic stem cells (hESC) and/or induced pluripotent stem (iPS) cells or a population of hESCs and/or a population of iPS cells with at least one lectin. The invention is also directed to a culture medium composition comprising at least one lectin. Further, the invention is directed to the use of a lectin in a method for culturing hESCs and/or iPS cells.

In one embodiment, the invention is directed to method for culturing hESCs and/or iPS cells with a lectin as a matrix and a definitive, serum- and feeder-free medium. The invention is also directed to a culture medium composition comprising at least one lectin and a definitive, serum- and feeder-free medium. Further, the invention is directed to the use of a lectin together with a definitive, serum- and feeder-free media in a method for culturing hESCs and/or iPS cells.

In one embodiment of the invention the lectin is a natural lectin originating and/or derived from a plant or an animal. In another embodiment, the lectin is a lectin derivative produced by biotechnology methods, such as recombinant technology.

In a further embodiment of the invention, the lectin is ECA (sometimes also called ESL) lectin isolated from *Erythrina cristagalli* seeds or an essentially similar lectin derivative produced biotechnologically, for example by gene technology means.

The invention is based on the use of at least one lectin, such as a plant lectin, in the culture of hESCs and/or iPS cells, preferably with a definitive, serum- and feeder-free medium.

BRIEF DESCRIPTION OF THE DRAWINGS

The following drawings are illustrative embodiments of the invention and are not meant to limit the scope of the invention as defined in the claims in any way.

FIG. 9 shows a list of lectins, corresponding to SEQ ID NOS:1-17, from top to bottom, respectively, whose amino acid sequences are highly homologous to that of ECA. Potential N-glycosylation sites have been indicated with highlighting. Lysine residue, which can be used to link the lectin to a surface, have been shown in bolded italics.

DETAILED DESCRIPTION OF THE INVENTION

Figure 1:
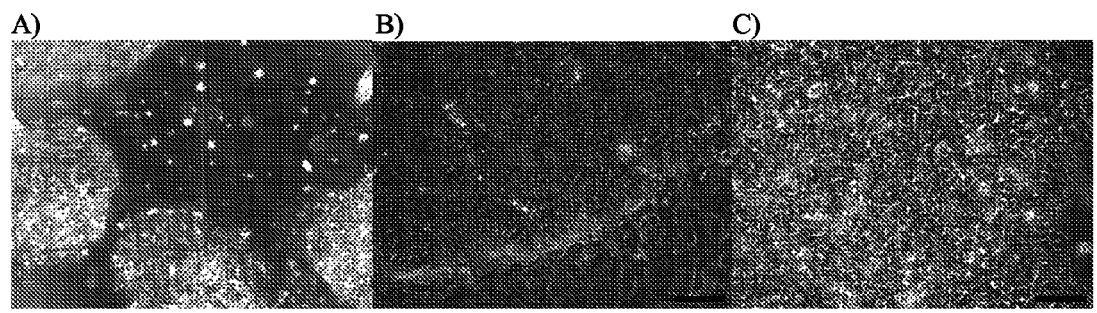
FIG. 1 shows the colonies of (A); FES 29 cells cultured on ECA-lectin for 6 passages (original magnification 4×), (B); FES 29 cells during passage 14 on ECA (magnification 10×) and (C); FES 30 cells cultured on ECA for 7 passages (magnification 10×) obtained in Example 1.

Human embryonic stem cells (hESCs) are derived from the inner cell mass of 3-5 day-old blastocysts. hESCs pose telomerase activity and express surface markers SSEA-3, SSEA-4, Tra-1-60 and Tra-1-81. They proliferate on continuous basis when maintained in an appropriate culture environment and differentiate both in vivo and in vitro into endo-, meso- and ectoderm. The differentiation is detected by formation of embryoid bodies in vitro and teratoma in vivo. hESCs are considered to be the building blocks for all types of cells in humans and thus have huge potential in applications of cell therapy and regenerative medicine. In technologies for harvesting hESCs the embryo is either destroyed or not, i.e. it remains alive. In one embodiment of the invention, the hESCs are harvested by a method that does not include the destruction of a human embryo. With regard to the safety of the transplantation applications of hESCs and the derivatives thereof, it is important to reduce or even eliminate the xenogenic contamination of these cells.

Induced pluripotent stem (iPS) cells are a type of pluripotent stem cell derived from principally any non-pluripotent or differentiated cell, such as an adult somatic cell, that has been induced to have all essential features of embryonic stem cells (ESC). The techniques were first described in human cells by Takahashi et al. in Cell 131: 861-872, 2007. They demonstrated the generation of iPS cells from adult dermal fibroblasts by transduction of four transcription factors: Oct3/4, Sox2, Klf4 and c-Myc. Later, it has been shown that there are also other ways to generate similar cells (Lowry and Plath, Nature Biotechnology 26(11): 1246-1248, 2008) and basically, in addition to fibroblasts, any cell, such as a blood cell, derived from an embryo, a newborn, a child, an grown-up and/or an adult may be converted to an iPS cell line. The iPS cells are considered to be identical to natural pluripotent stem cells, such as embryonic stem cells, in many respects. The iPS cells hold enormous promise as this way, cells having all features of an ESC can be produced without ethical problems. Also, ESC-like cells can be readily produced from affected individuals to study molecular mechanisms of diseases and to test therapeutic molecules. As for ESC lines, the culturing of iPS cells has turned out to be demanding and there is great need to more established and better defined culture conditions. As glycosylation and glycan-mediated interactions are cell-type specific, prior art from other cells does not teach the glycobiology of iPS cells. Thus, effects of lectins on growth of iPS cells are not predictable and/or obvious.

In one embodiment of the invention, the method, composition and use are directed to culturing hESCs. In another embodiment of the invention, the method, composition and use are directed to culturing iPS cells.

In a further embodiment of the invention, the method, composition and use are directed to culturing hESCs selected from cell lines FES 22, FES 29 and/or FES 30. In a still further embodiment of the invention, the method, composition and use are directed to culturing iPS cells selected from cell lines FiPS1-5, FiPS5-7, FiPS6-12 and/or FiPS6-14.

Lectins are sugar-binding proteins. They typically play a role in biological recognition phenomena involving cells and proteins. Most of the lectins are basically non-enzymatic in action and non-immune in origin. Lectins occur ubiquitously in nature. They may bind to a soluble carbohydrate or to a carbohydrate moiety which is a part of a more complex carbohydrate structure, such as a glycoprotein or glycolipid. They typically agglutinate certain animal cells and precipitate glycoconjugates. Lectins serve many different biological functions from the regulation of cell adhesion to glycoprotein synthesis and the control of protein levels in the blood. Lectins are also known to play important roles in the immune system by recognizing carbohydrates that are found exclusively on pathogens or that are inaccessible on host cells. Lectins could be derived from plants, such as legume plants like beans, grains and seeds. In addition, lectins having an animal origin are known. Legume lectins are one of the largest lectin families with more than 70 lectin family members.

Known lectins isolated from plants are, for example, Con A, LCA, PSA, PCA, GNA, HPA, WGA, PWM, TPA, ECA, DSA, UEA-1, PNA, SNA and MAA. Galectins are a family of lectins having mammalian origin. Lectins recognizing the "terminal N-acetyllactosamine" structure $(Fuc\alpha2)_n$ Galβ4GlcNAc, wherein n is 0 or 1, are a group of preferred lectins of the present invention. Lectins recognizing both the "terminal N-acetyllactosamine" structures wherein n is 0 and n is 1, is another preferred group of lectins. Optionally, the lectins do not essentially recognize sialylated and/or sulphated Galβ4GlcNAc-structures. These lectins include, in particular, ECA (*Erythrina cristagalli* lectin), DSA (*Datura Stramonium* lectin) and UEA-1 (Ulex europeaus agglutinin-I), as well as galectin lectins. In addition, a number of other natural lectins may have the specificity of recognizing and/or binding to the "terminal N-acetyllactosamine" structure. Furthermore, natural lectins can be mutagenized to improve their binding or to obtain binding specificity to the "terminal N-acetyllactosamine". These lectins recognize and/or bind to the "terminal N-acetyllactosamine" structure in an amount and/or extent adequate to fulfil the function for supporting the growth of the cell. A list of lectins, whose amino acid sequences are highly homologous to ECA is shown in FIG. 9. These lectins potentially have or may readily be biotechnologically modified by e.g. mutagenesis to have the same activity as ECA. ECA lectin refers also to variants of ECA that are modified in amino acid positions defined in FIG. 9, optionally with the amino acid variations shown in FIG. 9.

In one embodiment of the invention, the lectin is selected from ECA, UEA-1, galectin lectins and/or an essentially similar protein biotechnologically produced thereof. In another embodiment of the invention, the lectin is selected from lectins having characteristics substantially similar to ECA, UEA-1 and/or galectin lectins with regard to supporting the growth of the hESCs and/or iPS cells.

In one embodiment of the invention, the lectin is an animal-free galectin, that is, a recombinant lectin protein produced in cell culture system, preferably in a non-animal cell culture system.

In one embodiment of the invention, lectins include also oligosaccharide-binding protein domains and peptides derived from lectins. Preferably the lectins do not contain a non-lectin domain, such as an enzyme domain or toxic domain found, for example, in ricin agglutinin (RCA). The lectins of the present invention further include any polypeptide or equivalent being functionally a lectin. Antibodies and oligosaccharide-binding enzymes are examples of the proteins being functional lectins. Preferred enzymes include fucosidases and galactosidases modified to remove the catalytic activity. The antibodies include all types of natural and genetically engineered variants of immunoglobulin proteins. Preferred antibodies include blood group H type II and terminal N-acetyllactosamine binding antibodies.

In the present invention the term "terminal N-acetyllactosamine" refers to a neutral N-acetyllactosamine with a non-reducing terminal end; the neutral means that the structure is not modified by sialic acid or other acidic residues. Preferably terminal N-acetyllactosamine is non-substituted type II N-acetyllactosamine or its α2'-fucosylated variant structure (H-type II structure) according to formula $(Fuc\alpha 2)_n Gal\beta 4GlcNAc$, wherein n is 0 or 1.

The amount of lectin used in a solution is about 0.1-500 µg/ml, preferably about 5-200 µg/ml or about 10-150 µg/ml. The amount of lectin for immobilization of the cell culture surface is about 0.001-50 µg/cm$^2$, preferably from about 0.01-50 µg/cm$^2$ to about 0.1-30 µg/cm$^2$, more preferably about 0.3-10 µg/cm$^2$ for a lectin with Mw of about 50 kDa, or corresponding molar density per surface area used. In one embodiment, about 1-50 µg/cm$^2$, or about 5-40 µg/cm$^2$, preferably about 10-40 µg/cm$^2$ of lectin is used in a solution to coat a plastic cell culture surface. In one embodiment, the concentration in the coating solution is between about 50-200 µg/ml for a lectin with Mw of about 50 kDa or corresponding molar density per surface area used. In a specific embodiment, a plastic cell culture well with polystyre surface is coated by passive adsorption using about 140 µg/ml solution in amount of about 30 µg/cm$^2$ for a lectin with Mw of about 50 kDa.

The present invention relates to a method for culturing human embryonic stem cells (hESC) and/or induced pluripotent stem (iPS) cells or a hESC population and/or a iPS cell population with a lectin. The invention is also directed to a culture medium composition comprising a lectin as a matrix. Further, the invention is directed to the use of a lectin in a method for culturing hESCs and/or iPS cells.

In one embodiment, the invention is directed to a method for culturing hESCs and/or iPS cells with at least one lectin and to a culture medium composition comprising at least one lectin. Further, the invention is directed to the use of at least one lectin in a method for culturing hESCs and/or iPS cells.

In one embodiment of the invention, the method for culturing HECSs and/or iPS cells refers to a method for maintenance of the undifferentiated state of the cells i.e., a method that promotes the growth of the cells but does not induce the differentiation of the cells.

In one embodiment of the invention the lectin is a natural plant lectin such as ECA lectin and in another embodiment of the invention at least one of the lectins is ECA lectin.

In one embodiment, the invention is directed to method for culturing hESCs and/or iPS cells with a lectin as a culturing matrix and a definitive, serum- and feeder-free medium. The invention is also directed to a culture medium composition comprising a lectin and a definitive, serum- and feeder-free medium. Further, the invention is directed to the use of a lectin together with a definitive, serum- and feeder-free media in a method for culturing hESCs and/or iPS cells.

In another embodiment, the invention is directed to method for culturing hESCs and/or iPS cells with at least one lectin and a definitive, serum- and feeder-free medium and to a culture medium composition comprising at least one lectin and a definitive, serum- and feeder-free medium. Further, the invention is directed to the use of at least one lectin together with a definitive, serum- and feeder-free media in a method for culturing hESCs and/or iPS cells.

The method for culturing hESCs and/or iPS cells according to the present invention comprises forming a cell culture surface and/or matrix containing a lectin, inoculating an/or transferring the cells to the surface containing the lectin and culturing the cells up to the desired number of passages in the surface or matrix. The method for culturing hESCs and/or iPS cells according to the present invention comprises optionally a step for addition of a definitive or fully-defined, serum- and feeder-free medium into the culture system. The method may also contain additional and/or optional steps that are conventional to methods of culturing cells, such as washing, incubating and dividing the cell populations.

In one embodiment of the invention, the method for culturing hESCs and/or iPS cells comprises coating of cell culture plates or vessels with a lectin, inoculating an/or transferring the cells onto the lectin coated plates or vessels and culturing the cells up to the desired number of passages. In another embodiment of the invention, the method for culturing hESCs and/or iPS cells comprises coating of cell culture plates or vessels with a lectin, inoculating an/or transferring the cells onto the lectin coated plates or vessels, adding a definitive or fully-defined, serum- and feeder-free medium into the culture system and culturing the cells up to the desired number of passages.

A definitive or fully-defined, serum- and feeder-free medium is a medium that is specifically formulated for the uniform growth of hESCs and/or ESC-like cells, such as iPS cells and contains ingredients required for maintaining normal morphology, pluripotency and differentiation capability of hESCs and/or ESC-like cells, such as iPS cells. A definitive or fully-defined, serum- and feeder-free medium is free or essentially free of animal based and/or animal derived i.e., non-human ingredients. The serum- and feeder-free medium contains typically essential and non-essential amino acids, vitamins, growth factors, inorganic salts, trace elements and other components such as sugars, fatty acids and antibiotics. The relative amount of a specific ingredient depends on the quality and quantity of the other ingredients selected to the medium composition and on the manufacturer of the medium, for example. StemPro® hESC SFM, developed and sold by Invitrogen Corporation, US, and mTESR™, developed and sold by Stem Cell Technologies, US, are examples of this kind of a definitive, serum- and feeder-free medium developed for culturing of hESCs without feeder cells, but there are also many others with similar properties.

In a further embodiment of the invention, the definitive, serum- and feeder-free medium is StemPro® hESC SFM.

According to the present invention, a lectin is used as a sole culture matrix ingredient or it is added to a culture media applicable to the growth of hESCs and/or iPS cells or used with such a medium. The culture media can also be supplemented, for example, with a single or a plurality of growth factors selected from, for example, a WNT signaling agonist, TGF-b, bFGF, IL-6, SCF, BMP-2, thrombopoietin, EPO, IGF-1, IL-11, IL-5, Flt-3/Flk-2 ligand, fibronectin, LIF, HGF, NFG, angiopoietin-like 2 and 3, G-CSF, GM-CSF, Tpo, Shh, Wnt-3a, Kirre, or a mixture thereof.

In one embodiment of the invention, the hESCs and/or iPS cells are grown on a lectin, such as a plant lectin or galectin coated plate or vessel.

The hESCs and/or iPS cells cultured according to the present invention are not exposed to animal-derived material during their cultivation, at least not in such an extent than cells cultured according to the known methods using feeder cells, Matrigel™ and/or other animal-derived material.

The hESCs cultured according to the present invention have shown to have the typical characteristics of human embryonal stem cells, posing telomerase activity and expressing surface markers SSEA-3, Tra-1-60 and Tra-1-81. In addition, the cells have been shown to be able to differentiate by forming embryoid bodies and/or teratomas.

The iPS cells cultured according to the present invention have shown to express surface markers SSEA-3 and Tra-1-60 as well as express Oct-4 and Nanog genes, that are characteristics to pluripotent cells such as embryonal stem cells. They also were able to form teratomas, an essential indicator for pluripotency.

The method and the culture medium composition of the present invention provide means for culturing hESCs and/or iPS cells substantially free of xenogenic contamination. The hESCs, iPS cells and/or cell population(s) cultured according to the present invention are thus safe for the current and future transplantation applications.

The following examples represent illustrative embodiments of the invention without limiting the invention any way.

Example 1

Human Embryonic Stem Cell (hESC) Lines Cultured on ECA-Lectin Coated Plastic

Processes for generation of hESC lines from blastocyst stage of in vitro fertilized human embryos have been described previously in Thomson et al. (*Science*, 282:1145-1147, 1998). Cell lines FES 22, FES 29 and FES 30 were initially derived and cultured either on mouse embryonic fibroblasts feeders (MEFs; 12-13 pc fetuses of the ICR strain), or on human foreskin fibroblast feeder cells (HFFs; CRL-2429 ATCC, Mananas, USA) as disclosed in Mikkola et al. *BMC Dev Biol*, 6:40-51, 2006. All the lines were cultured in serum-free medium (KnockOut™ D-MEM; Gibco® Cell culture systems, Invitrogen, Paisley, UK) supplemented with 2 mM L-Glutamin/Penicillin streptomycin (Sigma-Aldrich), 20% KnockOut Serum Replacement (Gibco), 1× non-essential amino acids (Gibco), 0.1 mM β-mercaptoethanol (Gibco), 1× ITS (Sigma-Aldrich) and 4 ng/ml bFGF (Sigma/Invitrogen) on feeder cells, or on Matrigel™ (BD Biosciences) in the same medium (supplemented with additional 4 ng/ml bFGF) conditioned over night on MEFs. Passaging was done either mechanically or enzymatically using collagenase IV (Gibco).

ECA-Lectin Coating of Cell Culture Plates

ECA-lectin (EY laboratories, USA) was dissolved in phosphate buffered saline 140 μg/ml. Lectin dilution was sterile filtrated using Millex-GV syringe driven filter units (0.22 μm, SLGV 013 SL, Millipore, Ireland) and allowed to passively adsorb on cell culture plate by overnight incubation at +4° C. After incubation the wells were washed three times with phosphate buffered saline and stem cells were plated on them.

hESC Culturing on ECA-Lectin Coated Cell Culture Plates

The hESC lines (FES 22, FES 29, FES 30) were cultured at least three passages on Matrigel™ before transferring them onto ECA coated plates, FES 29 was transferred also directly from MEFs onto ECA coated plates in conditioned medium. All lines were maintained on Matrigel™ as controls. The growing cell aggregates were then passaged to new plates at 3-7 day intervals.

hESC Embryoid Body (EB) Formation

EBs were generated as previously described in Mikkola et al. (2006) with small modifications. Briefly, to induce the formation of EBs the confluent hESC colonies were first treated with 200 U/ml collagenase IV and transferred on non-adherent Petri dishes to form suspension cultures. The formed EBs were cultured in suspension for the next 10 days in standard culture medium (see above) without bFGF.

Teratoma Assay

In order to study teratoma formation about 200 000 morphologically good looking hESCs were injected into the testes of nude mice. The resulting tumors were harvested 8 weeks later and fixed with formalin for immunohistological examination as described in Mikkola et al. (2006).

Flow Cytometry hESCs were detached enzymatically and washed in 1% ultra pure BSA in PBS. Monoclonal antibodies against SSEA-3, Tra-1-60 and Tra-1-81 (1:50; gifts kindly provided by ESTOOLS www.estools.org) were used as markers for undifferentiated hESCs. Staining was performed according to manufacturer's instructions. FACS analysis was done with FACS Calibur machinery and CellquestPro software (Becton Dickinson).

Results

Three different hESC-lines, FES 22, FES 29 and FES 30, were is cultured on ECA-coated wells in MEF-conditioned medium up to 23 passages. The morphology of hESCs was similar to the control Matrigel cultures and hESCs looked undifferentiated after ECA-lectin passages (FIG. 1). Lines FES 29 and FES 30 were repeatedly successfully transferred from Matrigel to ECA-plates. FES 29 cells were also transferred onto ECA-lectin straight from feeder cells (MEFs).

Figure 2:
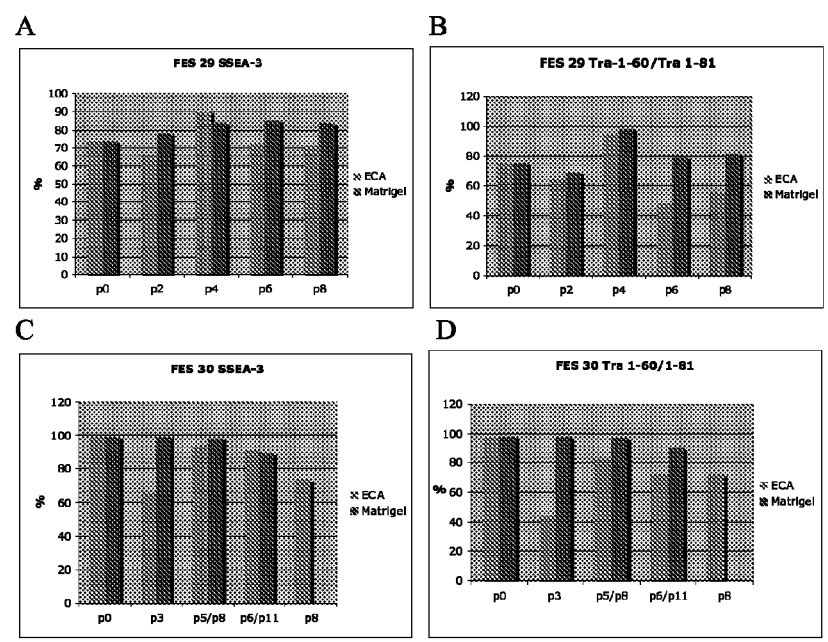
FIG. 2 shows the FACS analysis of the surface markers (A); SSEA3 and (B) Tra-1-60 (or Tra-1-81) expressions on FES 29 cells during ECA culture from the beginning of ECA culture (passage 0) to passage 8, and (C) SSEA3 and (D) Tra-1-60 (or Tra-1-81) expressions on FES 30 cells during ECA culture from the beginning of ECA culture (passage 0) to passage 8 obtained in Example 1. The surface marker expressions in the control Matrigel cultures are shown for comparison (p=passage ECA/Matrigel).

The expression of surface markers of undifferentiated hESCs (SSEA-3 and Tra-1-60/Tra-1-81) were analyzed every 2 or 3 passages by flow cytometry. The follow-up of the surface marker expression during the culture of FES 29 and FES 30 cells on ECA is shown in FIG. 2.

Figure 3:
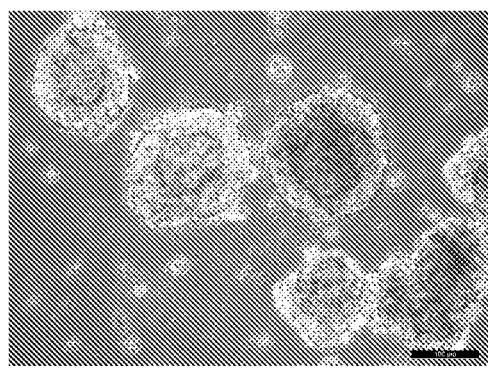
FIG. 3 shows the FES 29 cells cultured in suspension for EB formation after 9 passages on ECA described in Example 1.

The pluripotency of hESCs after several ECA passages was verified by their ability to form EBs in suspension culture or teratomas in nude mice. FES 30 cells cultured 23 passages on ECA and FES 29 cells cultured 4 passages on ECA formed teratoma-containing tissues from all three germ cell layers (data not shown). EBs were successfully formed from FES 29 and FES 30 cells after ECA-culture (FIG. 3).

Example 2

Culturing hESCs on ECA Lectin in Definitive Medium

Culturing hESCs

The FES 29 hESC line (see example 1) was cultured 14 passages on Matrigel™ before transferring the cells on ECA-lectin coated plates. The hESCs were cultured on ECA-lectin coated plates for 7 passages in MEF-conditioned medium and then changed to a definitive medium, StemPro® hESC SFM (Gibco, Invitrogen A10007-01, 2007/2008). Matrigel™ was used as a control. For enzymatic passaging the cells were exposed to 200 units/ml collagenase IV (Gibco) for 1-2 min at 37° C., washed once in PBS and dissociated by gently pipetting and plated on 2-3 new dishes.

hESC Embryoid Body (EB) Formation

EBs were generated as previously described in Mikkola et al. (2006). Briefly, to induce the formation of EBs the confluent hESC colonies were first treated with 200 U/ml collagenase IV and then transferred on non-adherent Petri dishes to form suspension cultures. The formed EBs were cultured in suspension for the next 10 days in the standard culture medium (see above) without bFGF.

Flow Cytometry hESCs were detached enzymatically and washed with 1% ultra pure BSA in PBS. Monoclonal antibodies against SSEA-3, Tra-1-60 and Tra-1-81 (1:50; gifts kindly provided by ESTOOLS www.estools.org) were used as markers for undifferentiated hESCs. Staining was performed according to manufacturer's instructions. FACS analysis was done with FACS Calibur machinery and CellQuestPro software (Becton Dickinson).

Figure 4:
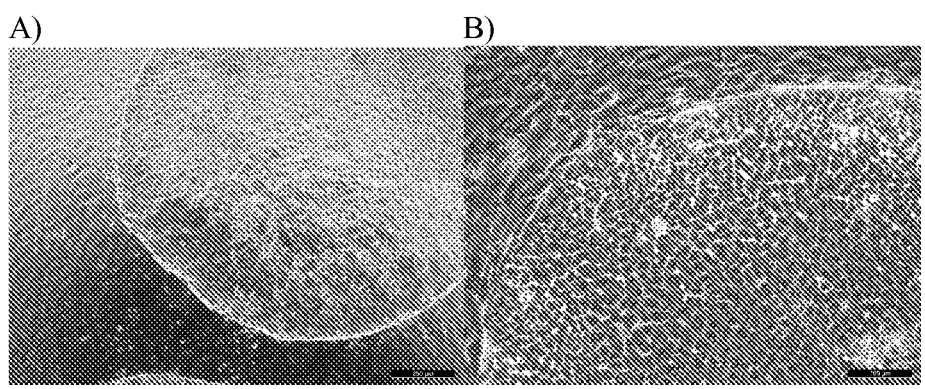
FIG. 4 shows the hESC colonies on ECA in StemPro® medium obtained in Example 2: (A) FES 29 cells cultured on ECA for 9 passages: first 7 passages in conditioned medium and then 2 passages in StemPro® definitive medium and (B) FES 29 cells during passage 3 in StemPro® medium on ECA passage 10.
Figure 5:
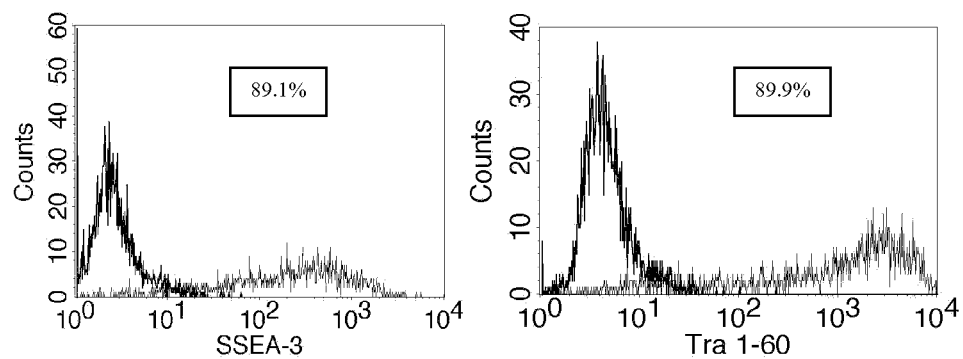
FIG. 5 shows the FACS-analysis of the expression of the two surface markers SSEA-3 and Tra-1-60 of undifferentiated hESCs described in Example 2. FES29-cells were cultured on ECA for 10 passages and with StemPro®-medium for the last 3 passages.
Figure 6:
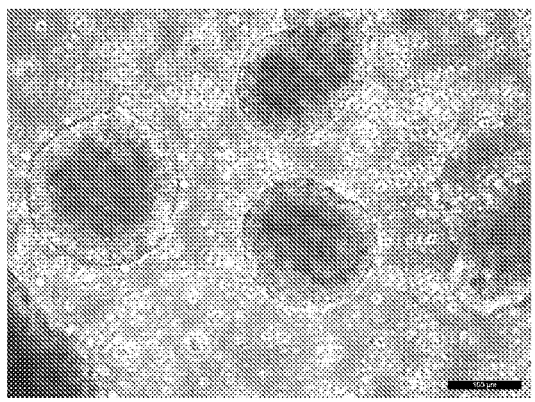
FIG. 6 shows the EBs formed from FES 29 cells after 12 ECA passages and 4 StemPro® passages obtained in Example 2.

Results hESCs, FES 29 line, were cultured on ECA-lectin for 7 passages with MEF-conditioned culture medium. In the 8$^{th}$ passage conditioned medium was changed to the commercial definitive medium, StemPro® hESC SFM. FES 29 cells maintained their undifferentiated state and pluripotency during up to 5 passages in definitive medium on ECA. In FIG. 4 the typical hESC colonies on ECA in the StemPro® medium are shown. FACS-analysis of the expression of surface markers of undifferentiated hESCs (SSEA-3 and Tra-1-60) is prerented in FIG. 5. EBs were formed after 12 passages on ECA and 4 passages in the StemPro® medium (FIG. 6).

Example 3

Culturing Induced Pluripotent Stem (iPS) Cells on ECA Lectin Coated Plastic

Culturing iPS Cells

Two lines of iPS cells were originated either from human embryonal lung fibroblasts or human (child under 18 years) foreskin fibroblasts with protocol modified from Okita et al. (*Nature*, 448:313-317, 2007) and Wernig et al. (*Nature*, 448: 318-324, 2007). FiPS1-5 and FiPS6-12 lines were cultured for 10 or 8 passages on MEFs before transferring them onto ECA or Matrigel™ coated dishes in MEF-conditioned medium. For enzymatic passaging the cells were subjected to 200 units/ml collagenase IV for 1-2 min at 37° C., washed once in PBS and dissociated by gently pipetting and plated on 2-3 new dishes.

hESC Embryoid Body (EB) Formation

EBs were generated as previously described in Mikkola et al. (2006). Briefly, to induce the formation of EBs the confluent cell colonies were first treated with 200 U/ml collagenase 1V and then transferred on non-adherent Petri dishes to form suspension cultures. The formed EBs were cultured in suspension for the next 10 days in standard culture medium (see above) without bFGF.

Figure 7:
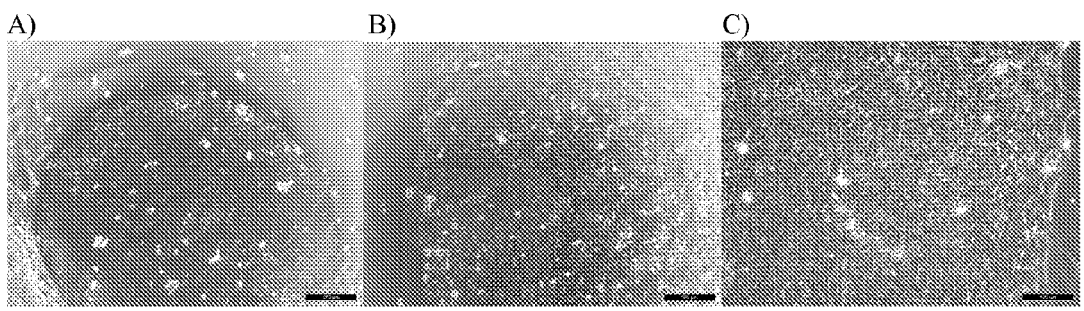
FIG. 7 shows (A) FiPS1-5 and (B-C) FiPS6-12 cell colonies after 5 passages on ECA-lectin in conditioned medium obtained in Example 3.
Figure 8:
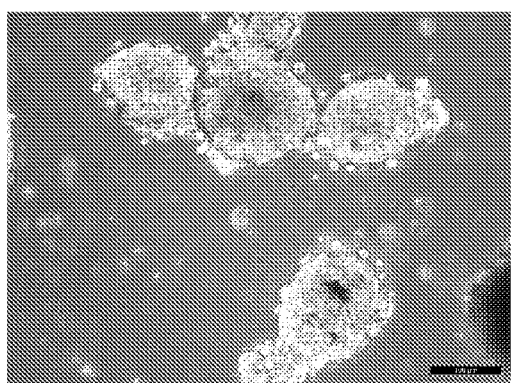
FIG. 8 shows EBs were formed from FiPS6-12 cells after 6 passages on ECA obtained in Example 3.

Results iPS-cells were cultured in similar in vitro conditions as hESCs. Two iPS cell-lines, FiPS1-5 and FiPS6-12, were transferred from MEFs (after passage 10 or 8, respectively) to Matrigel or to ECA-coated plates in MEF-conditioned medium. iPS cells were morphologically similar to hESCs in all culturing conditions (FIG. 7). EBs were formed from FiPS6-12 cells after 6 passages on ECA (FIG. 8).

Example 4

Culture of Induced Pluripotent Stem (iPS) Cell Line FiPS 6-14 on ECA

The iPS cell line was originated from human fibroblasts essentially as described by Takahashi et al (Cell 131:861-872), Okita et al. (Nature, 448:313-317, 2007) and Wernig et al. (Nature, 448:318-324, 2007). FiPS6-14 line was cultured on MEFs before transferring onto ECA or Matrigel™ coated dishes in MEF-conditioned medium. For enzymatic passaging the cells were subjected to 200 units/ml collagenase IV for 1-2 min at 37° C., washed twice in DMEM/F12 and dissociated by gently pipetting and plated on 2-3 new dishes.

Two parallel cultures, called here FiPS 6-14#p18 and FiPS 6-14#p21, were set up. The two cell cultures were cultured for 13 and 12 passages, respectively, on ECA in MEF-conditioned medium.

Cell surface expression of Tra-1-60 and SSEA-3 stem cell markers were analysed by flow cytometry. Briefly, the cells were detached enzymatically and washed in 1% ultra pure BSA in PBS-2 mM EDTA supplemented with 0.1% NaN$_3$. Monoclonal antibodies against SSEA-3 (1:20; provided by ES-TOOLS www.estools.org) and Tra-1-60 (1:20; TRA-1-60, Chemicon, cat. n:o MAB4360) were used. Secondary antibodies PE mouse anti-rat IgM (BD Pharmingen) and FITC rabbit anti-mouse IgM (Jackson ImmunoResearch) were used at 1:50 dilution and staining was performed according to manufacturer's instructions. Fluorescence-activated cell sorting (FACS) analysis was done with FACSAria apparatus and FACSDiva software (Becton Dickinson).

Figure 10:
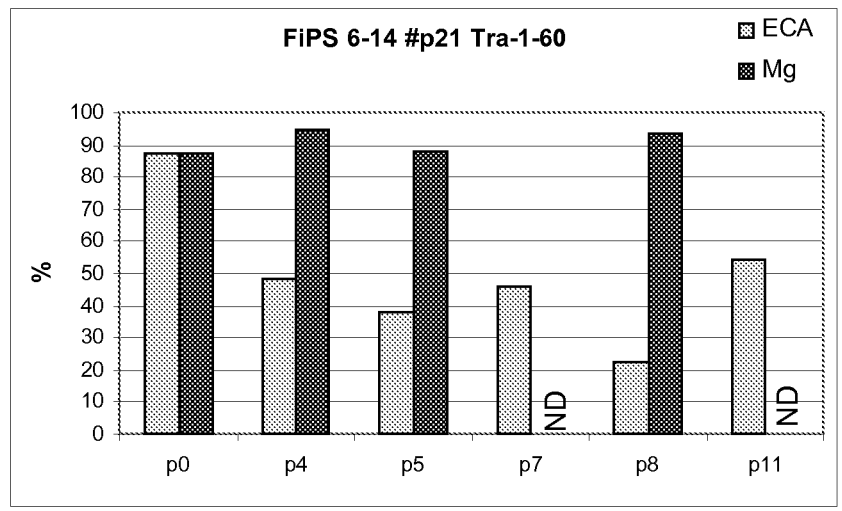
FIG. 10 shows surface expression of two markers for stem cellness, Tra-1-60 and SSEA-3, on the FiPS 6-14 cells as determined by standard FACS analysis. The expression of Tra-1-60 and SSEA-3 on FiPS 6-14 cells during ECA culture from the beginning of ECA culture (passage 0) to passage 11 (#p21, FIG. 10A) and to passage 12 (#p18, FIG. 10B) are shown. The surface marker expressions in the #p21 control Matrigel cultures are shown for comparison. p=passage.
Figure 10:
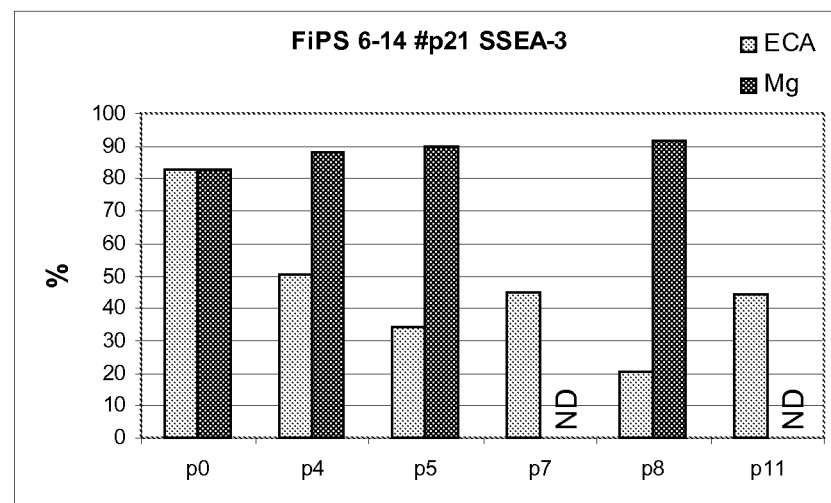
Figure 10:
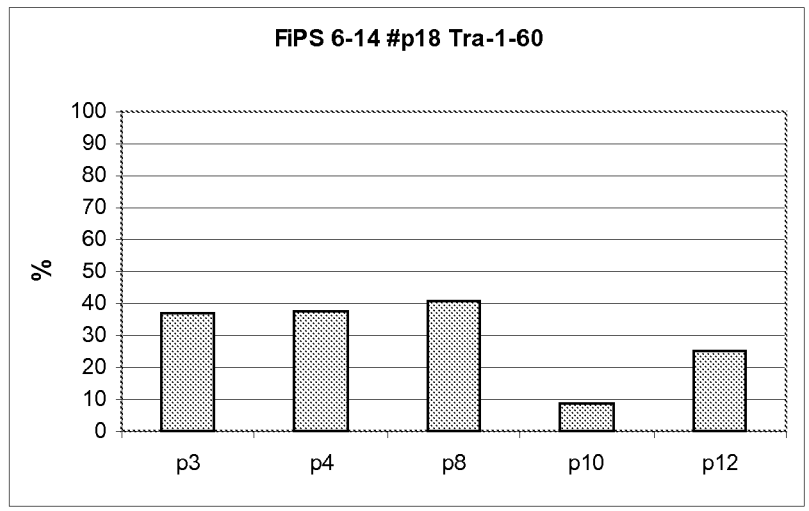
Figure 10:
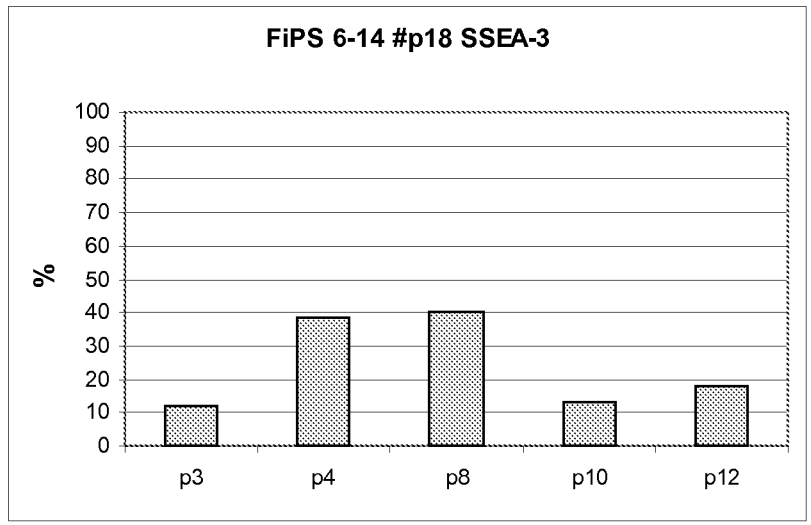

In FIG. 10 surface expression of two markers for stem cellness, Tra-1-60 and SSEA-3, on the FiPS 6-14 cells as determined by standard FACS analysis is shown. The results confirmed that the two parallel iPS cultures, FiPS 6-14#p21 and FiPS 6-14#p18, were positive for both ESC surface markers at least up to 11 and 12 passages, respectively. The average expression levels on the ECA surface were, however, about 30-40% of those determined for the cells cultured on Matrigel™ matrix (FiPS 6-14#p21, FIG. 10A).

The ability of ECA to support the growth of iPS cells in conditioned medium was tested using FiPS 6-14#p21 and StemPro™ medium. The cells were cultivated for 2 passages. They were morphologically normal as determined by CellIQ imaging and they expressed the stem cell markers as determined by FACS analysis: Tra-1-60 was found in 55.8% of the FiPS cells (control cells cultivated on MEF conditioned medium showed 54.2% staining) and SSEA-3 in 79.5% (control cells 44.5%).

Total mRNa was extracted from FiPS-6-14 cells using Nucleospin RNA II (Macherey Nagel) Rna extraction kit. Contaminating nuclear DNA was digested by rDNase (included by KIT) to remove DNA template.

Reverse transcription of RNA was carried out using High-Capacity cDNA reverse transcription kit (Applied Biosystems) according to manufactures protocol.

Quantitative PCR was carried out by using gene specific probes and primers purchased from Applied Biosystems. Taqman Gene expression assays: Nanog Hs02387400_g1, Tata Box binding protein Hs99999910_m1, Oct-4 Hs01895061_u1. Samples were run in duplicates or triplicates, containing 30 ng cDNA (calculated from RNA measurement) each. qPCR reactions were run by Abi Prism 7000 Sequence Detection systems, results analysed by sequence detection software, vesion 1.2.3. (Applied Biosystems).

Figure 11:
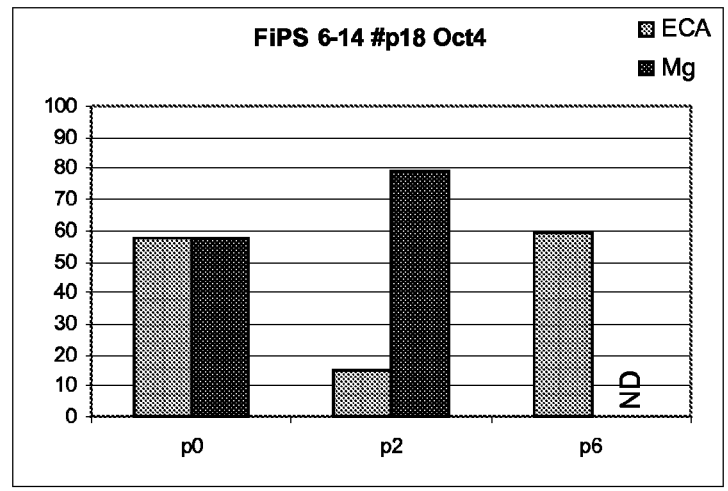
FIG. 11 shows mRNA expression levels of Oct-4 (both FiPS 6-14#p18 and FiPS 6-14#p21) and Nanog (FiPS 6-14#p21 only). The fold change in the expression levels of the genes were calculated with $2^{-\Delta\Delta C_T}$ method (Livak and Schmittgen, Methods 25, 2001). (A) Fold change of target gene (Oct-4 and Nanog) was calculated in relation to the expression of TBP endogenous control. Each value represents mean value of fold change (±S.E.) in gene expression relative to TBP. (B,C) Fold change in target gene was normalized to TBP endogenous control and to expression level at start of the growth (p0). Each value represents a mean±S.D. of duplicate or triplicate sample. Results from one of two separate runs are shown. p=passage.
Figure 11:
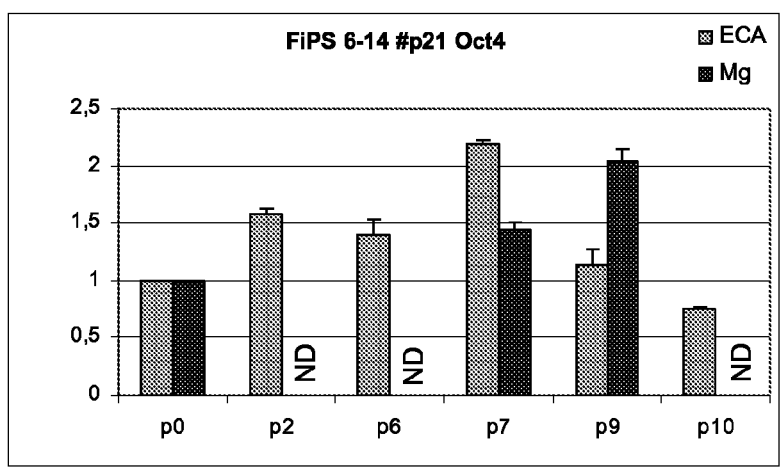
Figure 11:
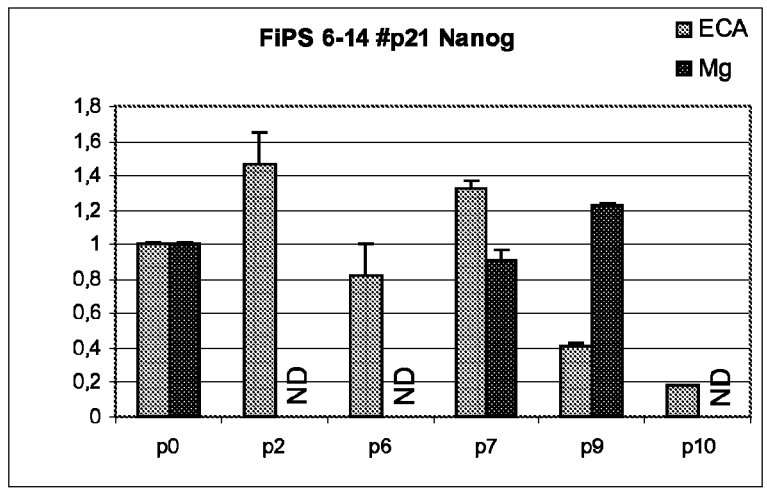

In FIG. 11 mRNA expression levels of Oct-4 (both FiPS 6-14#p18 and FiPS 6-14#p21) and Nanog (FiPS 6-14#p21 only), both established mRNA markers for stem cellness, are shown. The analysis confirmed that all the iPS cell samples up to 10 passages tested were positive for the two undifferentiated ESC marker genes. Furthermore, the iPS cells cultured up to 7 passages on ECA lectin express both marker genes at levels comparable to or even slightly higher than those observed for the cells cultured on the control Matrigel™ matrix (FiPS 6-14#p21, FIG. 10B). The expression profiles of the marker genes were very similar throughout the passages (FiPS 6-14#p21, FIG. 11B).

Karyotype of cell line FiPS 6-14#p18 was determined before and after culturing 13 passages on ECA and was found to be normal. The standard karyotyping was done by Medix, Ltd (Helsinki, Finland).

Example 5

Culture of Induced Pluripotent Stem (iPS) Cell Line FiPS 5-7 on ECA

The iPS cell line was originated from human fibroblasts essentially as described by Takahashi et al (Cell 131:861-872), Okita et al. (Nature, 448:313-317, 2007) and Wernig et al. (Nature, 448:318-324, 2007). FiPS6-14 line was cultured on MEFs before transferring onto ECA or Matrigel™ coated dishes in MEF-conditioned medium. For enzymatic passaging the cells were subjected to 200 units/ml collagenase IV for 1-2 min at 37° C., washed twice in DMEM/F12 and dissociated by gently pipetting and plated on 2-3 new dishes.

The cell line was cultivated on ECA in MEF-conditioned medium up to 27 passages. mRNA expression levels of Oct-4 and Nanog were determined to verify that the cells remained ESC-like cells.

Total mRNa was extracted from FiPS 5-7 cells using Nucleospin RNA II (Macherey Nagel) Rna extraction kit. Contaminating nuclear DNA was digested by rDNase (included by KIT) to remove DNA template.

Reverse transcription of RNA was carried out using High-Capacity cDNA reverse transcription kit (Applied Biosystems) according to manufactures protocol.

Quantitative PCR was carried out by using gene specific probes and primers purchased from Applied Biosystems, Taqman Gene expression assays: Nanog Hs02387400_g1, Tata Box binding protein Hs99999910_m1, Oct-4 Hs01895061_u1. Samples were run in duplicates or triplicates, containing 30 ng cDNA (calculated from RNA measurement) each. qPCR reactions were run by Abi Prism 7000 Sequence Detection systems, results analysed by sequence detection software, vesion 1.2.3. (Applied Biosystems).

Figure 12:
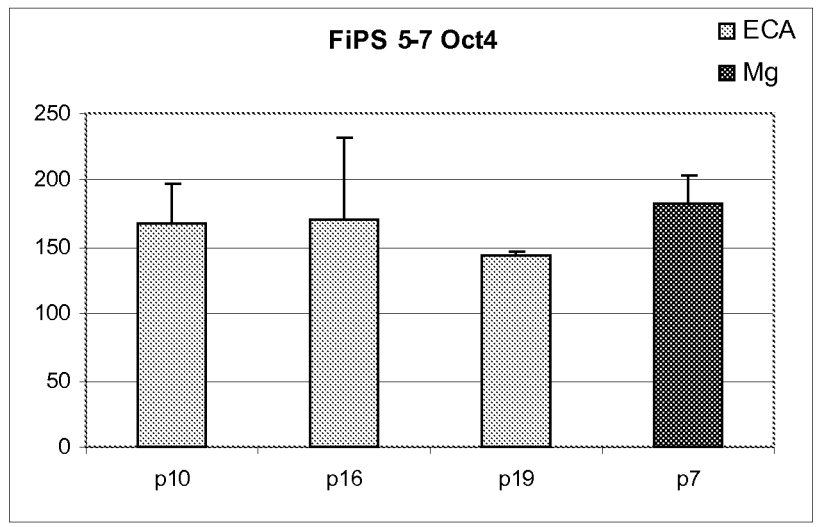
FIG. 12 shows mRNA expression levels of stem cell markers (A) OCT-4 and (B) Nanog. The fold change of target gene (Oct-4 and Nanog) was calculated in relation to the expression of TBP endogenous control with $2^{-\Delta\Delta C_T}$ method (Livak and Schmittgen, Methods 25, 2001). Each value represents mean value of fold change (±S.E.) in gene expression relative to TBP. p=passage.
Figure 12:
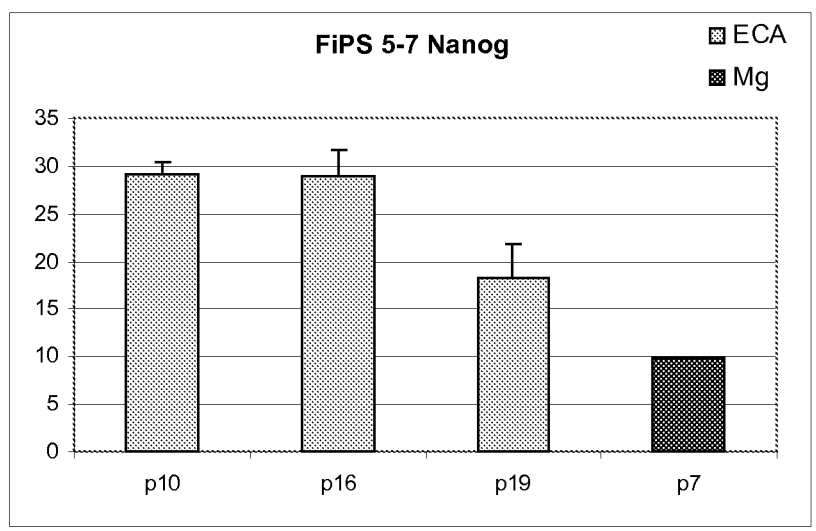

In FIG. 12 mRNA expression levels of stem cell markers Oct-4 (FIG. 12A) and Nanog (FIG. 12B) are shown. The stem cell marker expression from FiPS 5-7 cultured on ECA was analysed at passages 10, 16 and 19. After 10 passages on ECA, the cells were cultured on Matrigel for 7 further passages and the stem cell marker expression was analysed (p7 Mg in FIGS. 12A and 12B). The FiPS 5-7 cells cultured even up to 19 passages on ECA lectin expressed evidently both marker genes Oct-4 and Nanog. The expression levels of Oct-4 in FPS 5-7 cells cultured the first 10 passages on ECA followed by parallel cultivation for 6 passages on ECA and for 7 passages on the control Matrigel™ matrix were comparable as seen in FIG. 12A. Karyotype of cell line FiPS 5-7 was determined after culturing 12 passages on ECA and was found to be normal. The standard karyotyping was done by Medix, Ltd (Helsinki, Finland).

Example 6

Human Embryonic Stem Cell (hESC) Lines Cultured on ECA Lectin Coated Plastic Maintain Pluripotent Stage Materials and Methods Process for generation of hESC lines from blastocyst stage of in vitro fertilized human embryos have been described previously in Thomson et al. (Science, 282:1145-1147, 1998). The cell line FES 29 was initially derived and cultured on human foreskin fibroblast feeder cells (HFFs; CRL-2429 ATCC, Mananas, USA) as described in Mikkola et al. (2006). FES 29 was cultured either in commercial defined medium StemPro® hESC SFM (InVitrogen, Paisley, UK) or in conditioned serum-free medium (CM-medium): KnockOut™ D-MEM (Gibco® Cell culture systems, Invitrogen, Paisley, UK) supplemented with 2 mM L-Glutamin/Penicillin streptomycin (Sigma-Aldrich), 20% KnockOut Serum Replacement (Gibco), 1× non-essential amino acids (Gibco), 0.1 mM β-mercaptoethanol (Gibco), 1× ITS (Sigma-Aldrich) and 8 ng/ml bFGF (Sigma/invitrogen) conditioned over night on mouse fibroblast feeder cells. Cells were cultured either on Matrigel™ (cat n:o 356231 BD Biosciences) as a control culture or on ECA lectin (Ey Laboratories, tested product). Passaging was done enzymatically using collagenase IV (Gibco cat n:o 17104-019).

ECA-Coating of Cell Culture Plates

ECA lectin (EY laboratories, USA, Cat n:o L5901) was dissolved in phosphate buffered saline (PBS) 140 µg/ml. Lectin dilution was sterile filtrated using Millex-GV syringe driven filter units (0.22 µm, SLGV 013 SL, Millipore, Ireland) and allowed to passively adsorb on cell culture plate by overnight incubation at +4° C. After incubation the wells were washed three times with PBS and stem cells were plated on them.

Quantitative RT-PCR (qRT-PCR) Analysis

For qRT-PCR analysis FES 29 cell samples were harvested in lysis buffer included in RNA extraction kit (NucleoSpin RNA II, Macherey-Nagel, Duren, Germany) and stored at −70° C. Extracted RNA was purified (NucleoSpin RNA Cleanup-kit, Macherey-Nagel) and concentration of RNA was measured by spectrophotometer. Reverse transcription (RT) was performed using M-MLV-RTase (Promega) in final concentration of 5 U/µl for 90 minutes at +37° C. and RT enzyme was inactivated at +95° C. for 5 minutes. Quantitative PCR was performed with SYBR Green I (Molecular Probes/In Vitrogen) and Roche Applied Biosystem reagents (enzyme: AmpliTaq Cold™). Cyclophilin G was used as an endogenous control. VCR was performed with CAS-1200 pipetting robot and Corbett PCR machinery in 20 µl reaction volume.

Teratoma Assay

About 200000 morphologically good looking hESCs were injected into nude mice testis. The resulting tumors were harvested 8 weeks later and fixed with formalin for immuno-histological examination as described in Mikkola et al. (2006).

Results

Figure 13:
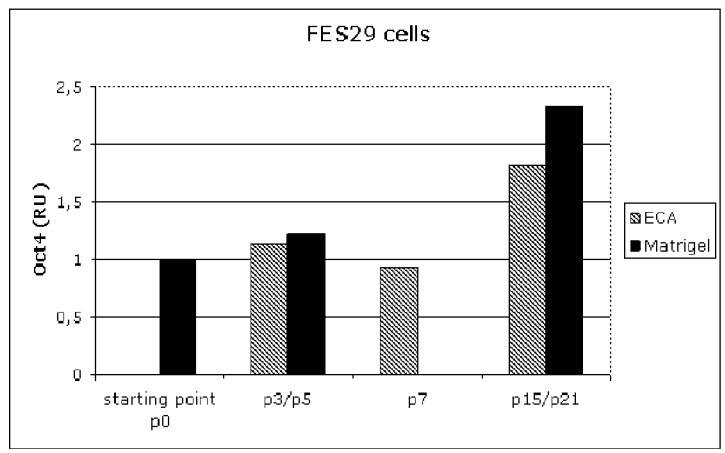
FIG. 13 shows the expression levels of Oct-4 mRNA in FES 29 cells as relative units (RU; $2^{-\Delta\Delta C_t}$) in which the threshold cycle (Ct) value of the marker gene was normalized to the Ct value of the housekeeping gene (Cyclophilin G; ΔCt). The differences were further compared to the starting point sample (ΔΔCt) and a calculation of $2^{-\Delta\Delta C_t}$ gave the relative value compared to the starting point (starting point sample gains value 1). p=passage.
Figure 14:
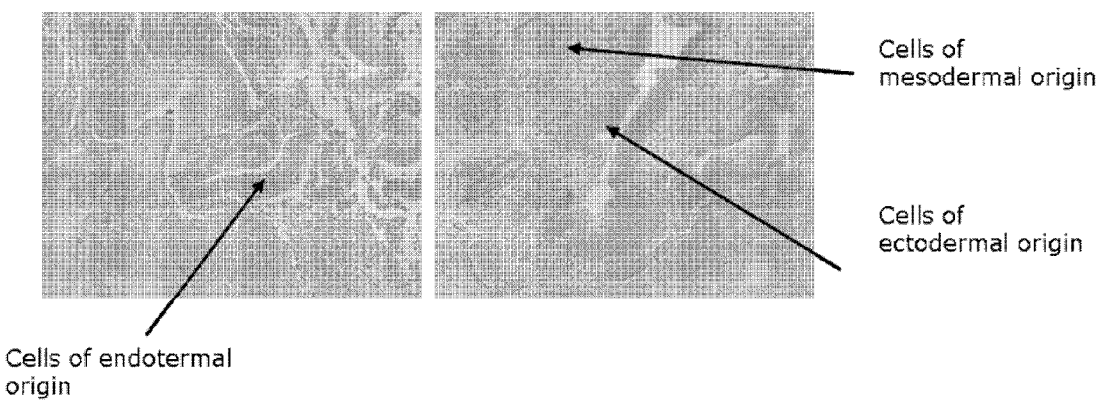
FIG. 14 shows photos of teratoma formed after transplantation of the FES 29 cells into nude mouse testis. Immunohistological examination showed tumour contained tissues representing all three germ layers, endoderm, mesoderm and ectoderm, as marked by arrows.

Quantitative RT-PCR analysis and teratoma assay have been used to demonstrate pluripotency of ECA-cultured FES 29 hESCs. For qRT-PCR the cells were cultured on ECA lectin (up to 15 passages) and on Matrigel™ (up to 21 passages) in the CM-medium and cell samples were collected for quantitative RT-PCR (qRT-PCR) every 2 or 3 passages. A selected part of the samples were analysed by qRT-PCR to determine the mRNA expression levels of Oct-4 which was used as the marker of undifferentiated and pluripotent hESCs. The mRNA expression of Oct-4 remained in comparable levels when culturing cells on ECA lectin compared to those cultured on Matrigel™ (FIG. 13). The expression of Oct-4 mRNA doubled in late passages but in the same way on both ECA and Matrigel™ matrices. These results suggest that hESCs cultured on ECA lectin remain in an undifferentiated stage. Pluripotency of the hESCs in vivo was assessed by the ability of the FES 29 cells to form teratomas in mice. For this, the hESCs were cultured for totally 15 passages on ECA lectin and the last 8 passages in StemPro medium before transplantation of the FES 29 cells into an immunodeficient mouse. The results of the teratoma assay (FIG. 14) confirmed that the hESCs cultivated on ECA lectin surface in defined medium kept their differentiation ability as demonstrated by formation of the three germ layer derivatives (endoterm, mesoderm and ectoderm).

The invention claimed is:

1. A method of culturing human induced pluripotent stem (iPS) in an undifferentiated state, wherein a human iPS cell or a human iPS cell population is contacted with at least one lectin immobilized on a surface, wherein said at least one lectin recognizes the structure (Fucα2)$_n$Galβ4GlcNAc, wherein n is 0 or 1, and wherein the human iPS cell or the human iPS cell population is cultured, thereby maintaining the human iPS cell or human iPS cell population in an undifferentiated state.

2. The method of claim 1, wherein the human iPS cell or the human iPS cell population is contacted with at least one lectin and with a definitive serum-free and feeder-free medium.

3. The method of claim 1, wherein the human iPS cell or the human iPS cell population is contacted with one lectin.

4. The method of claim 1, wherein the lectin is ECA, UEA-1, DSA, or galectin.

5. The method of claim 1, wherein the lectin has the specificity of ECA and recognizes the structure (Fucα2)$_n$Galβ4GlcNAc, wherein n is 0 or 1.

6. The method of claim 1, wherein the lectin is ECA and recognizes the structure (Fucα2)$_n$Gal4GlcNAc, wherein n is 0 or 1, and the human iPS cell population is cultured in either a fibroblast-conditioned media, or bFGF-containing media, thereby maintaining the human iPS in an undifferentiated state.

7. A culture medium composition for culturing induced pluripotent stem (iPS) cells, wherein the composition comprises at least one lectin as a matrix, said iPS cells and a definitive serum-free and feeder-free medium, and wherein the lectin recognizes the structure $(Fuc\alpha2)_n Gal\beta4GlcNAc$, wherein n is 0 or 1.

8. The composition of claim 7 wherein it comprises one lectin.

9. The composition of claim 7, wherein the lectin is ECA, UEA-1, DSA, or galectin.

10. The composition of claim 7, wherein the lectin has the specificity of ECA and recognizes the structure $(Fuc\alpha2)_n Gal\beta4GlcNAc$, wherein n is 0 or 1.

11. The composition of claim 7, wherein the lectin is ECA and recognizes the structure $(Fuc\alpha2)_n Gal\beta4GlcNAc$, wherein n is 0 or 1, said definitive serum-free and feeder-free medium is fibroblast-conditioned media, or bFGF-containing media, and said iPS cells are in an undifferentiated state.

* * * * *

UNITED STATES PATENT AND TRADEMARK OFFICE
CERTIFICATE OF CORRECTION

PATENT NO. : 8,703,488 B2
APPLICATION NO. : 13/003493
DATED : April 22, 2014
INVENTOR(S) : Ulla Impola et al.

It is certified that error appears in the above-identified patent and that said Letters Patent is hereby corrected as shown below:

ON THE TITLE PAGE:

At item (73), Assignees, change:

"(73) Assignees: Suomen Punainen Risti Veripalvelu, Helsinki (FI); Glykos Finland Oy, Helsinki (FI)"

to: -- (73) Assignee: Glykos Finland Oy, Helsinki (FI) --.

Signed and Sealed this
Second Day of September, 2014

Michelle K. Lee
*Deputy Director of the United States Patent and Trademark Office*

SEQUENCE LISTING

```
<160> NUMBER OF SEQ ID NOS: 17

<210> SEQ ID NO 1
<211> LENGTH: 242
<212> TYPE: PRT
<213> ORGANISM: Erythrina crista-galli

<400> SEQUENCE: 1

Val Glu Thr Ile Ser Phe Ser Phe Ser Glu Phe Glu Pro Gly Asn Asn
1               5                   10                  15

Asp Leu Thr Leu Gln Gly Ala Ala Ile Ile Thr Gln Ser Gly Val Leu
            20                  25                  30

Gln Leu Thr Lys Ile Asn Gln Asn Gly Met Pro Ala Trp Asp Ser Thr
        35                  40                  45

Gly Arg Thr Leu Tyr Thr Lys Pro Val His Ile Trp Asp Met Thr Thr
    50                  55                  60

Gly Thr Val Ala Ser Phe Glu Thr Arg Phe Ser Phe Ser Ile Glu Gln
65                  70                  75                  80

Pro Tyr Thr Arg Pro Leu Pro Ala Asp Gly Leu Val Phe Phe Met Gly
                85                  90                  95

Pro Thr Lys Ser Lys Pro Ala Gln Gly Tyr Gly Tyr Leu Gly Val Phe
            100                 105                 110

Asn Asn Ser Lys Gln Asp Asn Ser Tyr Gln Thr Leu Ala Val Glu Phe
        115                 120                 125

Asp Thr Phe Ser Asn Pro Trp Asp Pro Pro Gln Val Pro His Ile Gly
    130                 135                 140

Ile Asp Val Asn Ser Ile Arg Ser Ile Lys Thr Gln Pro Phe Gln Leu
145                 150                 155                 160

Asp Asn Gly Gln Val Ala Asn Val Val Ile Lys Tyr Asp Ala Ser Ser
                165                 170                 175

Lys Ile Leu Leu Ala Val Leu Val Tyr Pro Ser Ser Gly Ala Ile Tyr
            180                 185                 190

Thr Ile Ala Glu Ile Val Asp Val Lys Gln Val Leu Pro Glu Trp Val
        195                 200                 205

Asp Val Gly Leu Ser Gly Ala Thr Gly Ala Gln Arg Asp Ala Ala Glu
    210                 215                 220
```

```
Thr His Asp Val Tyr Ser Trp Ser Phe His Ala Ser Leu Pro Glu Thr
225                 230                 235                 240

Asn Asp

<210> SEQ ID NO 2
<211> LENGTH: 239
<212> TYPE: PRT
<213> ORGANISM: Erythrina corallodendron

<400> SEQUENCE: 2

Val Glu Thr Ile Ser Phe Ser Phe Ser Glu Phe Glu Pro Gly Asn Asp
1               5                   10                  15

Asn Leu Thr Leu Gln Gly Ala Ala Leu Ile Thr Gln Ser Gly Val Leu
            20                  25                  30

Gln Leu Thr Lys Ile Asn Gln Asn Gly Met Pro Ala Trp Asp Ser Thr
        35                  40                  45

Gly Arg Thr Leu Tyr Ala Lys Pro Val His Ile Trp Asp Met Thr Thr
50                  55                  60

Gly Thr Val Ala Ser Phe Glu Thr Arg Phe Ser Phe Ser Ile Glu Gln
65                  70                  75                  80

Pro Tyr Thr Arg Pro Leu Pro Ala Asp Gly Leu Val Phe Phe Met Gly
                85                  90                  95

Pro Thr Lys Ser Lys Pro Ala Gln Gly Tyr Gly Tyr Leu Gly Ile Phe
            100                 105                 110

Asn Asn Ser Lys Gln Asp Asn Ser Tyr Gln Thr Leu Gly Val Glu Phe
        115                 120                 125

Asp Thr Phe Ser Asn Pro Trp Asp Pro Pro Gln Val Pro His Ile Gly
130                 135                 140

Ile Asp Val Asn Ser Ile Arg Ser Ile Lys Thr Gln Pro Phe Gln Leu
145                 150                 155                 160

Asp Asn Gly Gln Val Ala Asn Val Val Ile Lys Tyr Asp Ala Ser Ser
                165                 170                 175

Lys Ile Leu His Ala Val Leu Val Tyr Pro Ser Ser Gly Ala Ile Tyr
            180                 185                 190

Thr Ile Ala Glu Ile Val Asp Val Lys Gln Val Leu Pro Glu Trp Val
        195                 200                 205

Asp Val Gly Leu Ser Gly Ala Thr Gly Ala Gln Arg Asp Ala Ala Glu
210                 215                 220

Thr His Asp Val Tyr Ser Trp Ser Phe Gln Ala Ser Leu Pro Glu
225                 230                 235

<210> SEQ ID NO 3
<211> LENGTH: 241
<212> TYPE: PRT
<213> ORGANISM: Erythrina variegata

<400> SEQUENCE: 3

Val Glu Thr Ile Ser Phe Ser Phe Ser Glu Phe Glu Ala Gly Asn Asp
1               5                   10                  15

Asn Leu Thr Leu Gln Gly Ala Ala Leu Ile Thr Gln Ser Gly Val Leu
            20                  25                  30

Gln Leu Thr Lys Ile Asn Gln Asn Gly Met Pro Ala Trp Asn Ser Thr
        35                  40                  45

Gly Arg Thr Leu Tyr Ser Lys Pro Val His Ile Trp Asp Lys Thr Thr
50                  55                  60

Gly Thr Val Ala Ser Phe Glu Thr Arg Phe Ser Phe Ser Ile Glu Gln
65                  70                  75                  80
```

```
Pro Tyr Thr Arg Pro Leu Pro Ala Asp Gly Leu Val Phe Phe Met Gly
                85                  90                  95

Pro Thr Lys Ser Lys Pro Ala Gln Gly Tyr Gly Tyr Leu Gly Val Phe
            100                 105                 110

Asn Asn Ser Lys Gln Asp Asn Ser Tyr Gln Thr Leu Ala Val Glu Phe
        115                 120                 125

Asp Thr Phe Ser Asn Pro Trp Asp Pro Pro Gln Gly Pro His Ile Gly
    130                 135                 140

Ile Asp Val Asn Ser Ile Arg Ser Ile Lys Thr Gln Pro Phe Gln Leu
145                 150                 155                 160

Asp Asn Gly Gln Val Ala Asn Val Val Ile Lys Tyr Asp Ala Ser Ser
                165                 170                 175

Lys Ile Leu His Ala Val Leu Val Tyr Pro Ser Asn Gly Ala Ile Tyr
            180                 185                 190

Thr Ile Ala Glu Ile Val Asp Val Lys Glu Val Leu Pro Glu Trp Val
        195                 200                 205

Asp Val Gly Leu Ser Gly Ala Thr Gly Ala Gln Arg Asp Ala Ala Glu
    210                 215                 220

Thr His Asp Val Tyr Ser Trp Ser Phe His Ala Ser Leu Pro Glu Thr
225                 230                 235                 240

Asn

<210> SEQ ID NO 4
<211> LENGTH: 242
<212> TYPE: PRT
<213> ORGANISM: Psophocarpus tetragonolobus

<400> SEQUENCE: 4

Met Lys Thr Ile Ser Phe Asn Phe Asn Gln Phe His Gln Asn Glu Glu
1               5                   10                  15

Gln Leu Lys Leu Gln Arg Asp Ala Arg Ile Ser Ser Asn Ser Val Leu
            20                  25                  30

Glu Leu Thr Lys Val Val Asn Gly Val Pro Thr Trp Asn Ser Thr Gly
        35                  40                  45

Arg Ala Leu Tyr Ala Lys Pro Val Gln Val Trp Asp Ser Thr Thr Gly
    50                  55                  60

Asn Val Ala Ser Phe Glu Thr Arg Phe Ser Phe Ser Ile Arg Gln Pro
65                  70                  75                  80

Phe Pro Arg Pro His Pro Ala Asp Gly Leu Val Phe Phe Ile Ala Pro
                85                  90                  95

Pro Asn Thr Gln Thr Gly Glu Gly Gly Gly Tyr Phe Gly Ile Tyr Asn
            100                 105                 110

Pro Leu Ser Pro Tyr Pro Phe Val Ala Val Glu Phe Asp Thr Phe Arg
        115                 120                 125

Asn Thr Trp Asp Pro Gln Ile Pro His Ile Gly Ile Asp Val Asn Ser
    130                 135                 140

Val Ile Ser Thr Lys Thr Val Pro Phe Thr Leu Asp Asn Gly Gly Ile
145                 150                 155                 160

Ala Asn Val Val Ile Lys Tyr Asp Ala Ser Thr Lys Ile Leu His Val
                165                 170                 175

Val Leu Val Phe Pro Ser Leu Gly Thr Ile Tyr Thr Ile Ala Asp Ile
            180                 185                 190

Val Asp Leu Lys Gln Val Leu Pro Glu Ser Val Asn Val Gly Phe Ser
        195                 200                 205
```

```
Ala Ala Thr Gly Asp Pro Ser Gly Lys Gln Arg Asn Ala Thr Glu Thr
        210                 215                 220

His Asp Ile Leu Ser Trp Ser Phe Ser Ala Ser Leu Pro Gly Thr Asn
225                 230                 235                 240

Glu Phe

<210> SEQ ID NO 5
<211> LENGTH: 238
<212> TYPE: PRT
<213> ORGANISM: Psophocarpus tetragonolobus

<400> SEQUENCE: 5

Glu Thr Gln Ser Phe Asn Phe Asp His Phe Glu Asn Ser Lys Glu
1               5                   10                  15

Leu Asn Leu Gln Arg Gln Ala Ser Ile Lys Ser Asn Gly Val Leu Glu
                20                  25                  30

Leu Thr Lys Leu Thr Lys Asn Gly Val Pro Val Trp Lys Ser Thr Gly
            35                  40                  45

Arg Ala Leu Tyr Ala Glu Pro Ile Lys Ile Trp Asp Ser Thr Thr Gly
        50                  55                  60

Asn Val Ala Ser Phe Glu Thr Arg Phe Ser Phe Asn Ile Thr Gln Pro
65                  70                  75                  80

Tyr Ala Tyr Pro Glu Pro Ala Asp Gly Leu Thr Phe Phe Met Val Pro
                85                  90                  95

Pro Asn Ser Pro Gln Gly Glu Asp Gly Gly Asn Leu Gly Val Phe Lys
            100                 105                 110

Pro Pro Glu Gly Asp Asn Ala Phe Ala Val Glu Phe Asp Thr Phe Gln
        115                 120                 125

Asn Thr Trp Asp Pro Gln Val Pro His Ile Gly Ile Asp Val Asn Ser
    130                 135                 140

Ile Val Ser Ser Lys Thr Leu His Phe Gln Leu Glu Asn Gly Gly Val
145                 150                 155                 160

Ala Asn Val Val Ile Lys Tyr Asp Ser Pro Thr Lys Ile Leu Asn Val
                165                 170                 175

Val Leu Ala Phe His Ser Val Gly Thr Val Tyr Thr Leu Ser Asn Ile
            180                 185                 190

Val Asp Leu Lys Gln Glu Phe Pro Asn Ser Glu Trp Val Asn Val Gly
        195                 200                 205

Leu Ser Ala Thr Thr Gly Tyr Gln Lys Asn Ala Val Glu Thr His Glu
    210                 215                 220

Ile Ile Ser Trp Ser Phe Thr Ser Ser Leu Gln Glu Thr Asn
225                 230                 235

<210> SEQ ID NO 6
<211> LENGTH: 268
<212> TYPE: PRT
<213> ORGANISM: Phaseolus lunatus

<400> SEQUENCE: 6

Gly Leu Ala Leu Phe Leu Val Leu Asn His Ala Asn Ser Thr Asp
1               5                   10                  15

Leu Phe Ser Phe Asn Phe Gln Thr Phe His Glu Ala Asn Leu Ile Leu
                20                  25                  30

Gln Gly Asn Ala Ser Val Ser Ser Gly Gln Leu Arg Leu Thr Glu
            35                  40                  45

Val Lys Ser Asn Gly Glu Pro Glu Val Ala Ser Leu Gly Arg Ala Phe
        50                  55                  60
```

```
Tyr Ser Ala Pro Ile Gln Ile Trp Asp Ser Thr Thr Gly Lys Val Ala
 65                  70                  75                  80

Ser Phe Ala Thr Ser Phe Thr Phe Asn Ile Leu Ala Pro Ile Leu Ser
             85                   90                  95

Asn Ser Ala Asp Gly Leu Ala Phe Ala Leu Val Pro Val Gly Ser Gln
            100                 105                 110

Pro Lys Phe Asn Gly Gly Phe Leu Gly Leu Phe Glu Asn Ala Thr Tyr
        115                 120                 125

Asp Pro Thr Ala Arg Thr Val Ala Val Glu Phe Asp Thr Cys Phe Asn
130                 135                 140

Leu Asp Trp Asp Pro Lys Gly Pro His Ile Gly Ile Asp Val Asn Ser
145                 150                 155                 160

Ile Lys Ser Ile Lys Thr Val Pro Trp Ser Leu Leu Asn Gly His Asn
                165                 170                 175

Ala Lys Val Leu Ile Thr Tyr Asp Ser Ser Thr Lys Leu Leu Val Ala
            180                 185                 190

Ser Leu Val Tyr Pro Ser Gly Ser Thr Ser Tyr Ile Ile Ser Glu Lys
        195                 200                 205

Val Asp Leu Lys Ser Val Leu Pro Glu Trp Val Asn Ile Gly Phe Ser
210                 215                 220

Ala Thr Ser Gly Leu Asn Lys Gly Asn Val Glu Thr His Asp Val Leu
225                 230                 235                 240

Ser Trp Ser Phe Ala Ser Lys Leu Ser Asp Gly Thr Pro Cys Glu Gly
                245                 250                 255

Leu Ser Leu Ala Asn Ile Val Leu Asn Lys Ile Leu
            260                 265

<210> SEQ ID NO 7
<211> LENGTH: 278
<212> TYPE: PRT
<213> ORGANISM: Phaseolus augusti

<400> SEQUENCE: 7

Met Ala Ser Ser Lys Phe Cys Thr Val Leu Ser Leu Ala Leu Phe Leu
 1               5                  10                  15

Val Leu Leu Thr His Ala Asn Ser Ala Glu Leu Phe Ser Phe Asn Phe
             20                  25                  30

Gln Thr Phe Asn Glu Ala Asn Leu Ile Leu Gln Gly Asn Ala Ser Val
             35                  40                  45

Ser Ser Ser Gly Gln Leu Arg Leu Thr Glu Val Lys Ser Asn Gly Val
         50                  55                  60

Pro Glu Val Ala Ser Leu Gly Arg Ala Phe Tyr Ser Ala Pro Ile Gln
 65                  70                  75                  80

Ile Trp Asp Ser Thr Thr Gly Lys Val Ala Ser Phe Ala Thr Ala Phe
                 85                  90                  95

Thr Phe Asn Ile Leu Ala Pro Ile Leu Ser Asn Ser Ala Asp Gly Leu
            100                 105                 110

Ala Phe Ala Leu Val Pro Val Gly Ser Gln Pro Lys Phe Asn Gly Gly
        115                 120                 125

Phe Leu Gly Leu Phe Gln Asn Val Thr Tyr Asp Pro Thr Ala Gln Thr
130                 135                 140

Val Ala Val Glu Phe Asp Thr Cys His Asn Leu Asp Trp Asp Pro Lys
145                 150                 155                 160

Gly Pro His Ile Gly Ile Asp Val Asn Ser Ile Lys Ser Ile Lys Thr
                165                 170                 175
```

```
Val Pro Trp Ser Leu Leu Asn Gly His Asn Ala Lys Val Leu Ile Thr
            180                 185                 190

Tyr Asp Ser Ser Thr Lys Leu Leu Val Ala Ser Leu Val Tyr Pro Ser
            195                 200                 205

Gly Ser Thr Ser Tyr Ile Ile Ser Glu Lys Val Glu Leu Lys Ser Val
        210                 215                 220

Leu Pro Glu Trp Val Asn Ile Gly Phe Ser Ala Thr Ser Gly Leu Asn
225                 230                 235                 240

Lys Gly Asn Val Glu Thr His Asp Val Leu Ser Trp Ser Phe Ala Ser
                245                 250                 255

Lys Leu Ser Asp Gly Thr Thr Cys Glu Gly Leu Ser Leu Ala Asn Ile
                260                 265                 270

Val Leu Asn Gln Ile Leu
                275

<210> SEQ ID NO 8
<211> LENGTH: 277
<212> TYPE: PRT
<213> ORGANISM: Phaseolus maculatus

<400> SEQUENCE: 8

Met Ala Ser Ser Asn Phe Ser Thr Val Leu Ser Leu Ala Leu Phe Leu
1               5                   10                  15

Val Leu Leu Thr His Ala Asn Ser Thr Asn Leu Phe Ser Phe Asn Phe
            20                  25                  30

Gln Lys Phe His Glu Pro Asn Leu Ile Leu Gln Gly Asn Ala Ser Val
        35                  40                  45

Ser Ser Ser Gly Gln Leu Arg Leu Thr Glu Val Lys Ser Asn Gly Glu
    50                  55                  60

Pro Glu Val Ala Ser Leu Gly Arg Ala Phe Tyr Ser Ala Pro Ile Gln
65                  70                  75                  80

Ile Trp Asp Asn Thr Thr Gly Asn Val Ala Ser Phe Ala Thr Ser Phe
                85                  90                  95

Thr Phe Asn Ile Leu Ser Pro Thr Ile Ser Lys Ser Ala Asp Gly Leu
            100                 105                 110

Ala Phe Ala Leu Val Pro Val Gly Ser Gln Pro Lys Thr Tyr Gly Gly
        115                 120                 125

Tyr Leu Gly Leu Phe Gln His Ala Thr Asn Asp Pro Thr Ala Gln Thr
    130                 135                 140

Val Ala Val Glu Phe Asp Thr Phe Phe Asn Arg Glu Trp Asp Pro Glu
145                 150                 155                 160

Gly His His Ile Gly Ile Asp Val Asn Ser Ile Lys Ser Met Lys Thr
                165                 170                 175

Val Pro Trp Asp Phe Leu Asn Gly His Asn Ala Glu Val Leu Ile Thr
            180                 185                 190

Tyr Asp Ser Ser Thr Asn Leu Leu Val Ala Ser Leu Val Tyr Pro Ser
            195                 200                 205

Gly Ala Met Ser Cys Ile Ser Glu Arg Val Val Leu Lys Ser Val Leu
        210                 215                 220

Pro Glu Trp Val Asn Ile Gly Phe Ser Ala Thr Ser Gly Leu Asn Lys
225                 230                 235                 240

Gly Tyr Val Glu Thr His Asp Val Leu Ser Trp Ser Phe Ala Ser Glu
                245                 250                 255
```

-continued

```
Leu Ser Ala Gly Thr Thr Ser Glu Gly Leu Ser Leu Ala Asn Ile Val
            260                 265                 270

Leu Asn Lys Ile Leu
        275

<210> SEQ ID NO 9
<211> LENGTH: 278
<212> TYPE: PRT
<213> ORGANISM: Phaseolus leptostachyus

<400> SEQUENCE: 9

Met Ala Ser Ser Asn Phe Ser Thr Val Phe Ser Leu Ala Leu Phe Leu
1               5                   10                  15

Val Leu Leu Thr Gln Ala Asn Ser Thr Asp Leu Phe Ser Phe Asn Phe
            20                  25                  30

Gln Lys Phe His Ser His Asn Leu Ile Leu Gln Gly Asp Ala Ser Val
        35                  40                  45

Ser Ser Ser Gly Gln Leu Arg Leu Thr Gly Val Lys Ser Asn Gly Glu
    50                  55                  60

Pro Lys Val Ala Ser Leu Gly Arg Val Phe Tyr Ser Ala Pro Ile Gln
65                  70                  75                  80

Ile Trp Asp Asn Thr Thr Gly Asn Val Ala Ser Phe Ala Thr Ser Phe
                85                  90                  95

Thr Phe Asn Ile Leu Ala Pro Thr Val Ser Lys Ser Ala Asp Gly Leu
            100                 105                 110

Ala Phe Ala Leu Val Pro Val Gly Ser Gln Pro Lys Ser Asp Gly Gly
        115                 120                 125

Tyr Leu Gly Leu Phe Glu Ser Ala Thr Tyr Asp Pro Thr Ala Gln Thr
    130                 135                 140

Val Ala Val Glu Phe Asp Thr Phe Phe Asn Gln Lys Trp Asp Pro Glu
145                 150                 155                 160

Gly Arg His Ile Gly Ile Asp Val Asn Ser Ile Lys Ser Val Lys Thr
                165                 170                 175

Ala Pro Trp Gly Leu Leu Asn Gly His Lys Ala Glu Ile Leu Ile Thr
            180                 185                 190

Tyr Asp Ser Ser Thr Asn Leu Leu Val Ala Ser Leu Val His Pro Ala
        195                 200                 205

Gly Ala Thr Ser His Ile Val Ser Glu Arg Val Glu Leu Lys Ser Val
    210                 215                 220

Leu Pro Glu Trp Val Ser Ile Gly Phe Ser Ala Thr Ser Gly Leu Ser
225                 230                 235                 240

Lys Gly Phe Val Glu Ile His Asp Val Leu Ser Trp Ser Phe Ala Ser
                245                 250                 255

Lys Leu Ser Asn Glu Thr Thr Ser Glu Gly Leu Ser Leu Ala Asn Ile
            260                 265                 270

Val Leu Asn Lys Ile Leu
        275

<210> SEQ ID NO 10
<211> LENGTH: 273
<212> TYPE: PRT
<213> ORGANISM: Phaseolus vulgaris
```

<400> SEQUENCE: 10

Met Ala Ser Ser Lys Leu Leu Ser Leu Ala Leu Phe Leu Val Leu Leu
1               5                   10                  15

Thr Leu Ala Asn Ser Ala Ser Glu Thr Ser Phe Ser Phe Gln Arg Phe
            20                  25                  30

Asn Glu Thr Asn Leu Ile Leu Gln Gly Asn Ala Ser Val Ser Ser Ser
        35                  40                  45

Gly Gln Leu Arg Leu Thr Asn Leu Asn Gly Asn Gly Glu Pro Arg Val
    50                  55                  60

Gly Ser Leu Gly Arg Ala Phe Tyr Ser Ala Pro Ile Gln Ile Trp Asp
65                  70                  75                  80

Lys Thr Thr Gly Thr Val Ala Ser Phe Ala Thr Ser Phe Thr Phe Asn
                85                  90                  95

Met Gln Val Pro Asn Asn Ala Gly Pro Ala Asp Gly Leu Ala Phe Ala
            100                 105                 110

Leu Val Pro Val Gly Ser Gln Pro Lys Asp Lys Gly Gly Phe Leu Gly
        115                 120                 125

Leu Phe Asp Gly Ser Asn Ser Asn Phe His Thr Val Ala Val Glu Phe
    130                 135                 140

Asp Thr Leu Tyr Asn Lys Asp Trp Asp Pro Arg Glu Arg His Ile Gly
145                 150                 155                 160

Ile Asp Val Asn Ser Ile Arg Ser Ile Lys Thr Thr Pro Trp Asn Phe
                165                 170                 175

Val Asn Gly Glu Asn Ala Glu Val Leu Ile Thr Tyr Asp Ser Ser Thr
            180                 185                 190

Lys Leu Leu Val Ala Ser Leu Val Tyr Pro Ser Gln Lys Thr Ser Phe
        195                 200                 205

Ile Val Ser Asp Thr Val Asp Leu Lys Ser Val Leu Pro Glu Trp Val
    210                 215                 220

Ser Val Gly Phe Ser Ala Thr Thr Gly Ile Asn Lys Gly Asn Val Glu
225                 230                 235                 240

Thr Asn Asp Val Leu Ser Trp Ser Phe Ala Ser Lys Leu Ser Asp Gly
                245                 250                 255

Thr Thr Ser Glu Gly Leu Asn Leu Ala Asn Leu Val Leu Asn Lys Ile
            260                 265                 270

Leu

<210> SEQ ID NO 11
<211> LENGTH: 253
<212> TYPE: PRT
<213> ORGANISM: Glycine max

<400> SEQUENCE: 11

Ala Glu Thr Val Ser Phe Ser Trp Asn Lys Phe Val Pro Lys Gln Pro
1               5                   10                  15

Asn Met Ile Leu Gln Gly Asp Ala Ile Val Thr Ser Ser Gly Lys Leu
            20                  25                  30

Gln Leu Asn Lys Val Asp Glu Asn Gly Thr Pro Lys Pro Ser Ser Leu
        35                  40                  45

Gly Arg Ala Leu Tyr Ser Thr Pro Ile His Ile Trp Asp Lys Glu Thr
    50                  55                  60

Gly Ser Val Ala Ser Phe Ala Ala Ser Phe Asn Phe Thr Phe Tyr Ala
65                  70                  75                  80

Pro Asp Thr Lys Arg Leu Ala Asp Gly Leu Ala Phe Phe Leu Ala Pro
                85                  90                  95

```
Ile Asp Thr Lys Pro Gln Thr His Ala Gly Tyr Leu Gly Leu Phe Asn
            100                 105                 110

Glu Asn Glu Ser Gly Asp Gln Val Ala Val Glu Phe Asp Thr Phe
        115                 120                 125

Arg Asn Ser Trp Asp Pro Pro Asn Pro His Ile Gly Ile Asn Val Asn
130                 135                 140

Ser Ile Arg Ser Ile Lys Thr Thr Ser Trp Asp Leu Ala Asn Asn Lys
145                 150                 155                 160

Val Ala Lys Val Leu Ile Thr Tyr Asp Ala Ser Thr Ser Leu Leu Val
                165                 170                 175

Ala Ser Leu Val Tyr Pro Ser Gln Arg Thr Ser Asn Ile Leu Ser Asp
            180                 185                 190

Val Val Asp Leu Lys Thr Ser Leu Pro Glu Trp Val Arg Ile Gly Phe
        195                 200                 205

Ser Ala Ala Thr Gly Leu Asp Ile Pro Gly Glu Ser His Asp Val Leu
210                 215                 220

Ser Trp Ser Phe Ala Ser Asn Leu Pro His Ala Ser Ser Asn Ile Asp
225                 230                 235                 240

Pro Leu Asp Leu Thr Ser Phe Val Leu His Glu Ala Ile
                245                 250

<210> SEQ ID NO 12
<211> LENGTH: 285
<212> TYPE: PRT
<213> ORGANISM: Robinia pseudoacacia

<400> SEQUENCE: 12

Met Ala Thr Ser Asn Leu Gln Thr Leu Lys Ser Leu Phe Phe Val Leu
1               5                   10                  15

Leu Ser Ile Ser Leu Thr Phe Phe Leu Leu Pro Asn Lys Val Asn
                20                  25                  30

Ser Thr Glu Ser Val Ser Phe Ser Phe Thr Lys Phe Val Pro Glu Glu
            35                  40                  45

Gln Asn Leu Ile Leu Gln Gly Asp Ala Gln Val Arg Pro Thr Gly Thr
        50                  55                  60

Leu Glu Leu Thr Lys Val Glu Thr Gly Thr Pro Ile Ser Asn Ser Leu
65                  70                  75                  80

Gly Arg Ala Leu Tyr Ala Ala Pro Ile Arg Ile Tyr Asp Asn Thr Thr
                85                  90                  95

Gly Asn Leu Ala Ser Phe Val Thr Ser Phe Ser Phe Asn Ile Lys Ala
            100                 105                 110

Pro Asn Arg Phe Asn Ala Ala Glu Gly Leu Ala Phe Phe Leu Ala Pro
        115                 120                 125

Val Asn Thr Lys Pro Gln Ser Pro Gly Gly Leu Leu Gly Leu Phe Lys
130                 135                 140

Asp Lys Glu Phe Asp Lys Ser Asn Gln Ile Val Ala Val Glu Phe Asp
145                 150                 155                 160

Thr Phe Phe Asn Glu Glu Trp Asp Pro Gln Gly Ser His Ile Gly Ile
                165                 170                 175

Asp Val Asn Ser Ile Asn Ser Val Lys Thr Thr Arg Phe Ala Leu Ala
            180                 185                 190

Asn Gly Asn Val Ala Asn Val Val Ile Thr Tyr Glu Ala Ser Thr Lys
        195                 200                 205

Thr Leu Thr Ala Phe Leu Val Tyr Pro Ala Arg Gln Thr Ser Tyr Ile
210                 215                 220
```

Val Ser Ser Val Val Asp Leu Gln Asp Val Leu Pro Gln Phe Val Asp
225                 230                 235                 240

Val Gly Phe Ser Ala Thr Thr Gly Leu Ser Glu Gly Leu Val Glu Ser
                245                 250                 255

His Asp Ile Leu Ser Trp Ser Phe His Ser Asn Leu Pro Asp Ser Ser
                260                 265                 270

Ser Asp Ala Leu Ala Asn Asn Ile Leu Arg Asp Phe Met
            275                 280                 285

<210> SEQ ID NO 13
<211> LENGTH: 286
<212> TYPE: PRT
<213> ORGANISM: Maackia amurensis

<400> SEQUENCE: 13

Ala Thr Ser Asn Ser Lys Pro Thr Gln Val Leu Leu Ala Thr Phe Leu
1               5                   10                  15

Thr Phe Phe Phe Leu Leu Leu Asn Asn Val Asn Ser Ser Asp Glu Leu
                20                  25                  30

Ser Phe Thr Ile Asn Asn Phe Val Pro Asn Glu Ala Asp Leu Leu Phe
            35                  40                  45

Gln Gly Glu Ala Ser Val Ser Ser Thr Gly Val Leu Gln Leu Thr Arg
    50                  55                  60

Val Glu Asn Gly Gln Pro Gln Gln Tyr Ser Val Gly Arg Ala Leu Tyr
65                  70                  75                  80

Ala Ala Pro Val Arg Ile Trp Asp Asn Thr Thr Gly Ser Val Ala Ser
                85                  90                  95

Phe Ser Thr Ser Phe Thr Phe Val Val Lys Ala Pro Asn Pro Thr Ile
                100                 105                 110

Thr Ser Asp Gly Leu Ala Phe Phe Leu Ala Pro Pro Asp Ser Gln Ile
            115                 120                 125

Pro Ser Gly Arg Val Ser Lys Tyr Leu Gly Leu Phe Asn Asn Ser Asn
    130                 135                 140

Ser Asp Ser Ser Asn Gln Ile Val Ala Val Glu Phe Asp Thr Tyr Phe
145                 150                 155                 160

Gly His Ser Tyr Asp Pro Trp Asp Pro Asn Tyr Arg His Ile Gly Ile
                165                 170                 175

Asp Val Asn Gly Ile Glu Ser Ile Lys Thr Val Gln Trp Asp Trp Ile
            180                 185                 190

Asn Gly Gly Val Ala Phe Ala Thr Ile Thr Tyr Leu Ala Pro Asn Lys
    195                 200                 205

Thr Leu Ile Ala Ser Leu Val Tyr Pro Ser Asn Gln Thr Ser Phe Ile
210                 215                 220

Val Ala Ala Ser Val Asp Leu Lys Glu Ile Leu Pro Glu Trp Val Arg
225                 230                 235                 240

Val Gly Phe Ser Ala Ala Thr Gly Tyr Pro Thr Gln Val Glu Thr His
                245                 250                 255

Asp Val Leu Ser Trp Ser Phe Thr Ser Thr Leu Glu Ala Asn Ser Asp
                260                 265                 270

Ala Ala Thr Glu Asn Asn Val His Ile Ala Arg Tyr Thr Ala
            275                 280                 285

<210> SEQ ID NO 14
<211> LENGTH: 258
<212> TYPE: PRT
<213> ORGANISM: Ulex europaeus -continued

<400> SEQUENCE: 14

```
Asn Leu Ser Asp Asp Leu Ser Phe Asn Phe Asp Lys Phe Val Pro Asn
1               5                   10                  15

Gln Lys Asn Ile Ile Phe Gln Gly Ala Ala Ser Val Ser Thr Thr Gly
            20                  25                  30

Val Leu Gln Val Thr Lys Val Ser Lys Pro Thr Thr Thr Ser Ile Gly
        35                  40                  45

Arg Ala Leu Tyr Ala Ala Pro Ile Gln Ile Trp Asp Ser Thr Thr Gly
    50                  55                  60

Lys Val Ala Ser Phe Ala Thr Ser Phe Ser Phe Val Val Lys Ala Asp
65                  70                  75                  80

Lys Ser Asp Gly Val Asp Gly Leu Ala Phe Phe Leu Ala Pro Ala Asn
                85                  90                  95

Ser Gln Ile Pro Ser Gly Ser Ser Ala Ser Met Phe Gly Leu Phe Asn
            100                 105                 110

Ser Ser Asp Ser Lys Ser Ser Asn Gln Ile Ile Ala Val Glu Phe Asp
        115                 120                 125

Thr Tyr Phe Gly Lys Ala Tyr Asn Pro Trp Asp Pro Asp Phe Lys His
    130                 135                 140

Ile Gly Ile Asp Val Asn Ser Ile Lys Ser Ile Lys Thr Val Lys Trp
145                 150                 155                 160

Asp Trp Arg Asn Gly Glu Val Ala Asp Val Val Ile Thr Tyr Arg Ala
                165                 170                 175

Pro Thr Lys Ser Leu Thr Val Cys Leu Ser Tyr Pro Ser Asp Glu Thr
            180                 185                 190

Ser Asn Ile Ile Thr Ala Ser Val Asp Leu Lys Ala Ile Leu Pro Glu
        195                 200                 205

Trp Val Ser Val Gly Phe Ser Gly Gly Val Gly Asn Ala Ala Glu Phe
    210                 215                 220

Glu Thr His Asp Ile Leu Ser Trp Tyr Phe Thr Ser Asn Leu Glu Ala
225                 230                 235                 240

Asn Asn Pro Ala Ala Met Glu Tyr Asn Asp Glu His Leu Ala Ser Phe
                245                 250                 255

Thr Ala
```

<210> SEQ ID NO 15
<211> LENGTH: 241
<212> TYPE: PRT
<213> ORGANISM: Ulex europaeus

<400> SEQUENCE: 15

```
Asp Asp Leu Ser Phe Lys Phe Lys Asn Phe Ser Gln Asn Gly Lys Asp
1               5                   10                  15

Leu Thr Phe Gln Gly Asn Ala Ser Val Leu Glu Thr Gly Val Leu Gln
            20                  25                  30

Leu Asn Lys Val Gly Asn Asn Leu Pro Asp Glu Thr Gly Gly Ile Ala
        35                  40                  45

Arg Tyr Ile Ala Pro Ile His Ile Trp Asn Asn Thr Gly Glu Val
    50                  55                  60

Ala Ser Phe Ile Thr Ser Phe Ser Phe Met Glu Thr Ser Ser Asn
65                  70                  75                  80

Pro Lys Ala Ala Thr Asp Gly Leu Thr Phe Phe Leu Ala Pro Pro Asp
                85                  90                  95

Ser Pro Leu Arg Arg Ala Gly Gly Tyr Phe Gly Leu Phe Asn Asp Thr
            100                 105                 110
```

```
Lys Cys Asp Ser Ser Tyr Gln Thr Val Ala Val Glu Pro Asp Thr Ile
            115                 120                 125

Gly Ser Pro Val Asn Ser Trp Asp Pro Gly Phe Pro His Ile Gly Ile
        130                 135                 140

Asp Val Asn Cys Val Ile Ser Ile Asn Ala Glu Arg Trp Asn Lys Arg
145                 150                 155                 160

Tyr Gly Ser Asn Asn Val Ala Asn Val Glu Ile Ile Tyr Glu Ala Ser
                165                 170                 175

Ser Lys Thr Leu Thr Ala Ser Leu Thr Tyr Pro Ser Asp Gln Thr Ser
            180                 185                 190

Ile Ser Val Thr Ser Ile Val Asp Leu Lys Glu Ile Leu Pro Glu Trp
        195                 200                 205

Val Ser Val Gly Phe Ser Gly Thr Thr Tyr Ile Gly Arg Gln Ala Thr
210                 215                 220

His Glu Val Leu Asn Trp Tyr Phe Ser Ser Thr Phe Asp Pro Asn Asn
225                 230                 235                 240

Asn

<210> SEQ ID NO 16
<211> LENGTH: 242
<212> TYPE: PRT
<213> ORGANISM: Ulex europaeus

<400> SEQUENCE: 16

Ser Asp Asp Leu Ser Phe Lys Phe Lys Asn Phe Ser Gln Asn Gly Lys
1               5                   10                  15

Asp Leu Ser Phe Gln Gly Asn Ala Ser Val Ile Glu Thr Gly Val Leu
            20                  25                  30

Gln Leu Asn Lys Val Gly Asn Asn Leu Pro Asp Glu Thr Gly Gly Ile
        35                  40                  45

Ala Arg Tyr Ile Ala Pro Ile His Ile Trp Asn Cys Asn Thr Gly Glu
    50                  55                  60

Leu Ala Ser Phe Ile Thr Ser Phe Ser Phe Phe Met Glu Thr Ser Ala
65                  70                  75                  80

Asn Pro Lys Ala Ala Thr Asp Gly Leu Thr Phe Phe Leu Ala Pro Pro
                85                  90                  95

Asp Ser Pro Leu Arg Arg Ala Gly Gly Tyr Phe Gly Leu Phe Asn Asp
            100                 105                 110

Thr Lys Cys Asp Ser Ser Tyr Gln Thr Val Ala Val Glu Phe Asp Thr
        115                 120                 125

Ile Gly Ser Pro Val Asn Phe Trp Asp Pro Gly Phe Pro His Ile Gly
    130                 135                 140

Ile Asp Val Asn Cys Val Lys Ser Ile Asn Ala Glu Arg Trp Asn Lys
145                 150                 155                 160

Arg Tyr Gly Leu Asn Asn Val Ala Asn Val Glu Ile Ile Tyr Glu Ala
                165                 170                 175

Ser Ser Lys Thr Leu Thr Ala Ser Leu Thr Tyr Pro Ser Asp Gln Thr
            180                 185                 190

Ser Ile Ser Val Thr Ser Ile Val Asp Leu Lys Glu Ile Leu Pro Glu
        195                 200                 205

Trp Val Ser Val Gly Phe Ser Gly Ser Thr Tyr Ile Gly Arg Gln Ala
    210                 215                 220

Thr His Glu Val Leu Asn Trp Tyr Phe Thr Ser Thr Phe Ile Asn Thr
225                 230                 235                 240

Asn Ser
```

```
<210> SEQ ID NO 17
<211> LENGTH: 292
<212> TYPE: PRT
<213> ORGANISM: Styphnolobium japonicum

<400> SEQUENCE: 17

Met Ala Thr Ser Asn Ser Arg Pro His Leu Leu Gln Thr His Lys Pro
1               5                   10                  15

Phe Ser Val Val Leu Ala Ile Ser Ile Thr Phe Phe Leu Leu Leu Leu
            20                  25                  30

Asn Lys Val Asn Ser Ala Glu Ile Leu Ser Pro Ser Phe Pro Lys Phe
                35                  40                  45

Ala Ser Asn Gln Glu Asp Leu Leu Leu Gln Gly Asp Ala Leu Val Ser
    50                  55                  60

Ser Lys Gly Glu Leu Gln Leu Thr Thr Val Glu Asn Gly Val Pro Ile
65                  70                  75                  80

Trp Asn Ser Thr Gly Arg Ala Leu Tyr Tyr Ala Pro Val His Ile Trp
                85                  90                  95

Asp Lys Ser Thr Gly Arg Val Ala Ser Phe Ala Thr Ser Phe Ser Phe
            100                 105                 110

Val Val Lys Ala Pro Val Ala Ser Lys Ser Ala Asp Gly Ile Ala Phe
            115                 120                 125

Phe Leu Ala Pro Pro Asn Asn Gln Ile Gln Gly Pro Gly Gly His
    130                 135                 140

Leu Gly Leu Phe His Ser Ser Gly Tyr Asn Ser Ser Tyr Gln Ile Ile
145                 150                 155                 160

Ala Val Asp Phe Asp Thr His Ile Asn Ala Trp Asp Pro Asn Thr Arg
                165                 170                 175

His Ile Gly Ile Asp Val Asn Ser Ile Asn Ser Thr Lys Thr Val Thr
            180                 185                 190

Trp Gly Trp Gln Asn Gly Glu Val Ala Asn Val Leu Ile Ser Tyr Gln
        195                 200                 205

Ala Ala Thr Glu Thr Leu Thr Val Ser Leu Thr Tyr Pro Ser Ser Gln
    210                 215                 220

Thr Ser Tyr Ile Leu Ser Ala Ala Val Asp Leu Lys Ser Ile Leu Pro
225                 230                 235                 240

Glu Trp Val Arg Val Gly Phe Thr Ala Ala Thr Gly Leu Thr Thr Gln
                245                 250                 255

Tyr Val Glu Thr His Asp Val Leu Ser Trp Ser Phe Thr Ser Thr Leu
            260                 265                 270

Glu Thr Gly Asp Cys Gly Ala Lys Asp Asp Asn Val His Leu Val Ser
        275                 280                 285

Tyr Ala Phe Ile
    290
```